US008404870B2

(12) United States Patent
Cluzeau et al.

(10) Patent No.: US 8,404,870 B2
(45) Date of Patent: Mar. 26, 2013

(54) ((2S,4R)-4,6-DIHYDROXYTETRAHYDRO-2H-PYRAN-2-YL)METHYL CARBOXYLATE AND PROCESS FOR THE PRODUCTION THEREOF

(75) Inventors: Jerome Cluzeau, Ljubljana (SI); Zdenko Casar, Ljubljana (SI); Peter Mrak, Ljubljana (SI); Matej Oslaj, Ljubljana (SI); Gregor Kopitar, Ljubljana (SI)

(73) Assignee: LEK Pharmaceuticals D.D., Ljubljana (SI)

( * ) Notice: Subject to any disclaimer, the term of this patent is extended or adjusted under 35 U.S.C. 154(b) by 152 days.

(21) Appl. No.: 12/864,445

(22) PCT Filed: Jan. 20, 2009

(86) PCT No.: PCT/EP2009/050583
§ 371 (c)(1),
(2), (4) Date: Oct. 25, 2010

(87) PCT Pub. No.: WO2009/092702
PCT Pub. Date: Jul. 30, 2009

(65) Prior Publication Data
US 2011/0046375 A1    Feb. 24, 2011

(30) Foreign Application Priority Data
Jan. 23, 2008 (EP) .................................. 08100845

(51) Int. Cl.
*C07D 301/27* (2006.01)
(52) U.S. Cl. ....................................................... 549/417
(58) Field of Classification Search .................. 435/125
See application file for complete search history.

(56) References Cited

U.S. PATENT DOCUMENTS
7,094,594 B2 *  8/2006  Nishiyama et al. .......... 435/280

FOREIGN PATENT DOCUMENTS
| AU | 2004200957 A1 | 3/2004 |
| CH | 683613 A5 | 4/1994 |
| GB | 1503773 | 3/1978 |
| JP | 2005-229858 A | 9/2005 |
| WO | WO 01/94337 A1 | 12/2001 |
| WO | WO 2005/092867 A2 | 10/2005 |
| WO | WO 2005/118794 A2 | 12/2005 |
| WO | WO 2006/134482 A1 | 12/2006 |
| WO | WO 2007/039287 A1 | 4/2007 |

OTHER PUBLICATIONS

M.D. Groaning et al., 39 Tetrahedron Letters, 5485-5488 (1998).*
Chih-Yuan Chuang et al., Electronic Effects on the Regio- and Enantioselectivity of the Asymmetric Aminohydroxylation of O-Substituted 4-Hydroxy-2-butenoates, Chirality, 2002, 14, 151-162.
Shigeto Negi et al., Synthesis and Staructure-Activity Relations of New [(E0 or (Z) 3-Substituted Carbamoyloxy]-1-Propenyl Cephalosporins, The Journal of Antibiotics, 1994, 47, (12), 1526-1540.
Harrie J.M. Gijsen et al., Unprecedented Asymmetric Aldol Reactions with Three Aldehyde Substrates Catalyzed by 2-Deoxyribose-5-phosphate Aldolase, J. Am. Chem. Soc., 1994, 116, 8422-8423.
Junjie Liu et al., Sequential aldol condensation catalyzed by DERA mutant Ser238Asp and a formal total synthesis of atorvastatin, Tetrahedron Letters, 2004, 45, 2439-2441.
William A. Greenberg et al., Development of an efficient, scalable, aldolase-catalyzed process for enantioselective synthesis of stain intermediates, PNAS, 2004, 101, (16), 5788-5793.
John D. Prugh et al., Synthesis and Utilization of the Chiral Synthon Methyl 3-O-Benzyl-2,4,6-trideoxy-6-iodo-D-erythro-hexopyranoside in the Synthesis of a Potent HMG-CoA Reductase Inhibitor, J. Org. Chem., 1986, 51,648-657.
Harrie J.M. Gijsen et al., Sequential Three-and Four-Substrate Aldol Reactions Catalyzed by Aldolases, J. Am. Chem. Soc., 1995, 117, (29), 7585-7591.
William J. Bailey et al., Pyrolysis of Esters. V. Mechanism of 1,4-Elimination, J. Org. Chem., 1956, 21, (3), 328-331.
Joseph Sambrook et al., Molecular Cloning: A Laboratory Manual, 3 Ed., Cold Spring Harbor Laboratory Press, 1989.
L.J. Brzezinski et al., The asymmetric Baylis-Hillman reaction as a template in organic synthesis, Tetrahedron, 1997, 53 (48), 16432.
John D, Sutherland et al., Synthesis and Solution Structures of Aminoacyl Compounds of Potential Prebiotic Significance, Tetrahedron Letters 1998, 39, 3299-3302.
Grace Desantis et al., Structure-Based Mutagenesis Approaches Toward Expanding the Substrate Specificity of D-2Deoxyribose-5-phosphate Aldolase, Bioorganic & Medicinal Chemistry, 2003, 11, 43-52.

* cited by examiner

*Primary Examiner* — James O Wilson
*Assistant Examiner* — Alexander R Pagano
(74) *Attorney, Agent, or Firm* — Arent Fox LLP

(57) ABSTRACT

The present invention relates to ((2S,4R)-4,6-dihydroxytetrahydro-2H-pyran-2-yl)methyl carboxylates and a process for the production thereof. Furthermore, the present invention relates to a process for the production of statins and in particular of Rosuvastatin and derivates thereof, wherein the above mentioned compounds are used as intermediates.

24 Claims, 1 Drawing Sheet

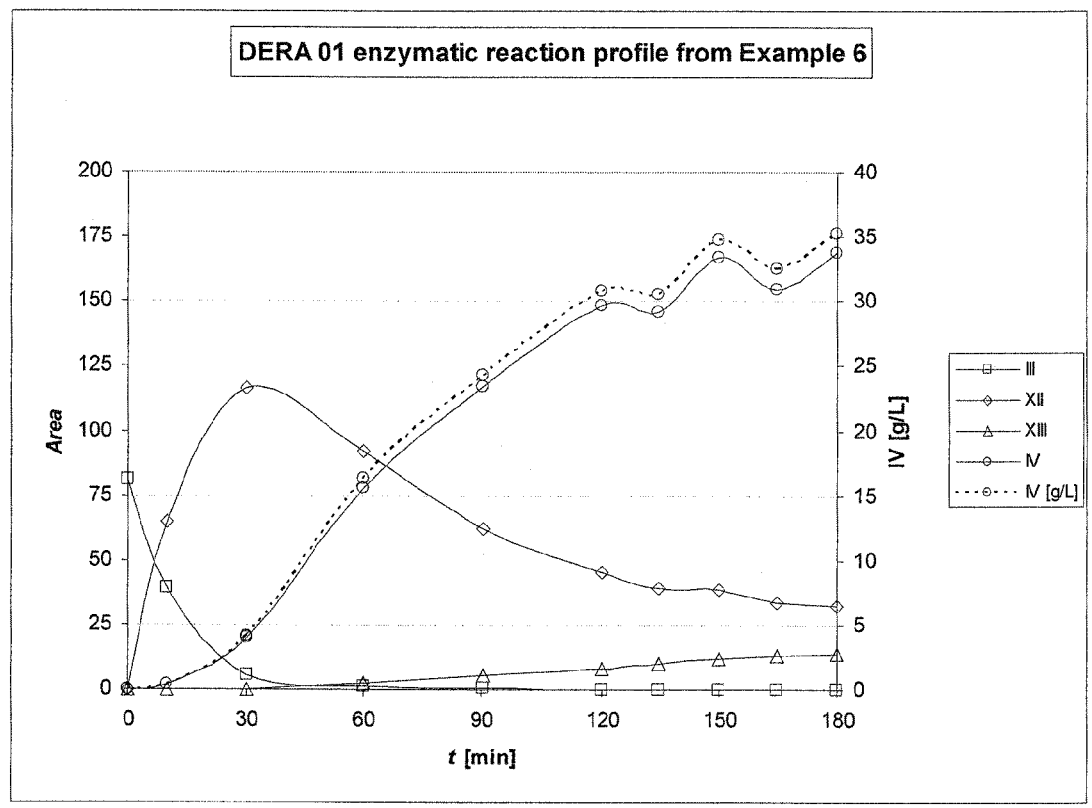

SEQUENCE LISTING

<160> NUMBER OF SEQ ID NOS: 49

<210> SEQ ID NO 1
<211> LENGTH: 780
<212> TYPE: DNA
<213> ORGANISM: Escherichia coli

<400> SEQUENCE: 1

```
atgactgatc tgaaagcaag cagcctgcgt gcactgaaat tgatggacct gaccaccctg      60
aatgacgacg acaccgacga gaaagtgatc gccctgtgtc atcaggccaa aactccggtc     120
ggcaataccg ccgctatctg tatctatcct cgctttatcc cgattgctcg caaaactctg     180
aaagagcagg gcaccccgga aatccgtatc gctacggtaa ccaacttccc acacggtaac     240
gacgacatcg acatcgcgct ggcagaaacc cgtgcggcaa tcgcctacgg tgctgatgaa     300
gttgacgttg tgttcccgta ccgcgcgctg atggcgggta acgagcaggt tggttttgac     360
ctggtgaaag cctgtaaaga ggcttgcgcg gcagcgaatg tactgctgaa agtgatcatc     420
gaaaccggcg aactgaaaga cgaagcgctg atccgtaaag cgtctgaaat ctccatcaaa     480
gcgggtgcgg acttcatcaa aacctctacc ggtaaagtgg ctgtgaacgc gacgccggaa     540
agcgcgcgca tcatgatgga agtgatccgt gatatgggcg tagaaaaaac cgttggtttc     600
aaaccggcgg gcggcgtgcg tactgcggaa gatgcgcaga aatatctcgc cattgcagat     660
gaactgttcg gtgctgactg ggcagatgcg cgtcactacc gctttggcgc ttccagcctg     720
ctggcaagcc tgctgaaagc gctgggtcac ggcgacggta agagcgccag cagctactaa     780
```

<210> SEQ ID NO 2
<211> LENGTH: 259
<212> TYPE: PRT
<213> ORGANISM: Escherichia coli

<400> SEQUENCE: 2

```
Met Thr Asp Leu Lys Ala Ser Ser Leu Arg Ala Leu Lys Leu Met Asp
1               5                   10                  15

Leu Thr Thr Leu Asn Asp Asp Asp Thr Asp Glu Lys Val Ile Ala Leu
            20                  25                  30

Cys His Gln Ala Lys Thr Pro Val Gly Asn Thr Ala Ala Ile Cys Ile
        35                  40                  45

Tyr Pro Arg Phe Ile Pro Ile Ala Arg Lys Thr Leu Lys Glu Gln Gly
    50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
                100                 105                 110

Gly Asn Glu Gln Val Gly Phe Asp Leu Val Lys Ala Cys Lys Glu Ala
```

```
              115                 120                 125
Cys Ala Ala Ala Asn Val Leu Leu Lys Val Ile Ile Glu Thr Gly Glu
            130                 135                 140

Leu Lys Asp Glu Ala Leu Ile Arg Lys Ala Ser Glu Ile Ser Ile Lys
145                 150                 155                 160

Ala Gly Ala Asp Phe Ile Lys Thr Ser Thr Gly Lys Val Ala Val Asn
                165                 170                 175

Ala Thr Pro Glu Ser Ala Arg Ile Met Met Glu Val Ile Arg Asp Met
            180                 185                 190

Gly Val Glu Lys Thr Val Gly Phe Lys Pro Ala Gly Gly Val Arg Thr
        195                 200                 205

Ala Glu Asp Ala Gln Lys Tyr Leu Ala Ile Ala Asp Glu Leu Phe Gly
    210                 215                 220

Ala Asp Trp Ala Asp Ala Arg His Tyr Arg Phe Gly Ala Ser Ser Leu
225                 230                 235                 240

Leu Ala Ser Leu Leu Lys Ala Leu Gly His Gly Asp Gly Lys Ser Ala
                245                 250                 255

Ser Ser Tyr

<210> SEQ ID NO 3
<211> LENGTH: 663
<212> TYPE: DNA
<213> ORGANISM: Unknown
<220> FEATURE:
<223> OTHER INFORMATION: Description of Unknown: Cloned polynucleotide

<400> SEQUENCE: 3
atgaatatcg cgaaaatgat cgatcatacg ctgctcaaac cggaagcgac agaacaacaa      60
atcgtgcaac tgtgcacgga agcaaagcaa tacggctttg ctgccgtgtg cgtcaaccca     120
acgtgggtga aaacggcggc gcgcgagctt tccggcacgg atgtccgcgt ctgcacggtc     180
atcggctttc cacttggggc aacgacgccg gaaacaaagg cgtttgaaac aacgaacgcc     240
atcgaaaacg cgctcgcga agtcgacatg gtgatcaaca tcggcgcgtt aaaaagcggg      300
caagacgagc ttgtcgagcg cgacattcgt gcggttgtcg aagcggcggc tgcagggcg      360 cttgtcaaag tgatcgttga aacggcgctt ttgaccgatg aggaaaaagt gcgcgcctgc     420
cagctcgcag tgaaagccgg cgctgattat gtgaaaacgt cgaccgggtt ttccggcgga     480
ggtgcgacgg tggaggatgt ggcgctgatg cggaaaacgg tcggcgacag agcaggcgtc     540
aaagcatcag gcgcgtccg tgactggaaa accgctgagg cgatgatcaa cgccggcgcg     600
acgcgcatcg gcacaagctc tggggtggcg atcgtcaccg gcgggacggg ccgcgctgac     660
tac                                                                   663

<210> SEQ ID NO 4
<211> LENGTH: 663
<212> TYPE: DNA
<213> ORGANISM: Unknown
<220> FEATURE:
<223> OTHER INFORMATION: Description of Unknown: Cloned polynucleotide

<400> SEQUENCE: 4
atgaacatcg cgaaaatgat cgatcacacc ctgctgaaac cggaagcgac cgaacagcag      60
attgttcagc tgtgcaccga agcgaaacag tatggttttg cggcggtgtg tgttaatccg     120
acctgggtta aaaccgcggc gcgtgaactg agcggcaccg atgttcgtgt gtgcaccgtg     180
attggttttc cgctgggtgc gaccaccccg gaaaccaaag cgtttgaaac caccaacgcg     240
```

```
attgaaaatg gtgcgcgcga agtggatatg gtgattaaca tcggcgcgct gaaaagcggt    300
caggatgaac tggttgaacg cgatattcgt gcggttgttg aagcggcggc gggtcgcgcg    360
ctggttaaag tgattgtgga accgcgctg ctgaccgatg aagaaaaagt gcgtgcctgt     420
cagctggcgg ttaaagcggg tgcggattac gttaaaacca gcaccggttt tagcggtggt    480
ggtgcgaccg ttgaagatgt tgcgctgatg cgtaaaaccg ttggtgatcg tgcgggtgtg    540
aaagcgagcg gtggtgttcg cgattggaaa accgcggaag cgatgattaa tgcgggcgcg    600
acccgtattg gcaccagcag cggtgttgcg attgttaccg gtggcaccgg tcgtgcggat    660
tat                                                                   663

<210> SEQ ID NO 5
<211> LENGTH: 221
<212> TYPE: PRT
<213> ORGANISM: Unknown
<220> FEATURE:
<223> OTHER INFORMATION: Description of Unknown: Testek polypeptide

<400> SEQUENCE: 5

Met Asn Ile Ala Lys Met Ile Asp His Thr Leu Leu Lys Pro Glu Ala
1               5                   10                  15

Thr Glu Gln Gln Ile Val Gln Leu Cys Thr Glu Ala Lys Gln Tyr Gly
            20                  25                  30

Phe Ala Ala Val Cys Val Asn Pro Thr Trp Val Lys Thr Ala Ala Arg
        35                  40                  45

Glu Leu Ser Gly Thr Asp Val Arg Val Cys Thr Val Ile Gly Phe Pro
    50                  55                  60

Leu Gly Ala Thr Thr Pro Glu Thr Lys Ala Phe Glu Thr Thr Asn Ala
65                  70                  75                  80

Ile Glu Asn Gly Ala Arg Glu Val Asp Met Val Ile Asn Ile Gly Ala
                85                  90                  95

Leu Lys Ser Gly Gln Asp Glu Leu Val Glu Arg Asp Ile Arg Ala Val
            100                 105                 110

Val Glu Ala Ala Ala Gly Arg Ala Leu Val Lys Val Ile Val Glu Thr
        115                 120                 125

Ala Leu Leu Thr Asp Glu Glu Lys Val Arg Ala Cys Gln Leu Ala Val
    130                 135                 140

Lys Ala Gly Ala Asp Tyr Val Lys Thr Ser Thr Gly Phe Ser Gly Gly
145                 150                 155                 160

Gly Ala Thr Val Glu Asp Val Ala Leu Met Arg Lys Thr Val Gly Asp
                165                 170                 175

Arg Ala Gly Val Lys Ala Ser Gly Gly Val Arg Asp Trp Lys Thr Ala
            180                 185                 190

Glu Ala Met Ile Asn Ala Gly Ala Thr Arg Ile Gly Thr Ser Ser Gly
        195                 200                 205

Val Ala Ile Val Thr Gly Gly Thr Gly Arg Ala Asp Tyr
    210                 215                 220

<210> SEQ ID NO 6
<211> LENGTH: 666
<212> TYPE: DNA
<213> ORGANISM: Oceanobacillus iheyensis

<400> SEQUENCE: 6
atggatttag ctaaatatat tgatcatact caattaaaac cagatactac aaaacaaagt    60
attgtaaaaa ttgtggaaga ggcaaaacaa catgaatttg cttcagtatg tgttaatcca    120
```

```
cactgggttt cttactgtta taatgaatta aaagatacac cagttaaagt ttgtacagta      180
attggattcc cattaggagc cacttctact gaaacgaaaa ttttttgaaac caatcaggct      240 attgctgatg gtgctacaga agtagacatg gtaattaatg tcggtgaatt aaaatcgaat      300
aatgatgctt tgttgaaaaa agacatccgt gctgttgttg aagcagcaaa aggtaaagct      360
ttaacaaaag tgataattga aacaagtctt ttaacagaag atgaaaaagt acgtgcttgt      420
aaattagcaa aaaatgcaga ggctgactat gtaaaaactt ctactgggtt ctctggtggc      480
ggcgcaactg ttgaggatat tcgcttaatg cgagagacag taggacctga aatgggagtg      540
aaagcatctg gtggtgttcg tgatttagag caaacagaag caatgattga agctggagca      600
actagaattg gagctagttc tggggtagcg attgtctcag agaacaagg tacatcagat      660 tactaa                                                                  666
```

<210> SEQ ID NO 7
<211> LENGTH: 221
<212> TYPE: PRT
<213> ORGANISM: Oceanobacillus iheyensis

<400> SEQUENCE: 7

```
Met Asp Leu Ala Lys Tyr Ile Asp His Thr Gln Leu Lys Pro Asp Thr
1               5                   10                  15

Thr Lys Gln Ser Ile Val Lys Ile Val Glu Glu Ala Lys Gln His Glu
            20                  25                  30

Phe Ala Ser Val Cys Val Asn Pro His Trp Val Ser Tyr Cys Tyr Asn
        35                  40                  45

Glu Leu Lys Asp Thr Pro Val Lys Val Cys Thr Val Ile Gly Phe Pro
    50                  55                  60

Leu Gly Ala Thr Ser Thr Glu Thr Lys Ile Phe Glu Thr Asn Gln Ala
65                  70                  75                  80

Ile Ala Asp Gly Ala Thr Glu Val Asp Met Val Ile Asn Val Gly Glu
                85                  90                  95

Leu Lys Ser Asn Asn Asp Ala Phe Val Glu Lys Asp Ile Arg Ala Val
            100                 105                 110

Val Glu Ala Ala Lys Gly Lys Ala Leu Thr Lys Val Ile Ile Glu Thr
        115                 120                 125

Ser Leu Leu Thr Glu Asp Glu Lys Val Arg Ala Cys Lys Leu Ala Lys
    130                 135                 140

Asn Ala Glu Ala Asp Tyr Val Lys Thr Ser Thr Gly Phe Ser Gly Gly
145                 150                 155                 160

Gly Ala Thr Val Glu Asp Ile Arg Leu Met Arg Glu Thr Val Gly Pro
                165                 170                 175

Glu Met Gly Val Lys Ala Ser Gly Gly Val Arg Asp Leu Glu Gln Thr
            180                 185                 190

Glu Ala Met Ile Glu Ala Gly Ala Thr Arg Ile Gly Ala Ser Ser Gly
        195                 200                 205

Val Ala Ile Val Ser Gly Glu Gln Gly Thr Ser Asp Tyr
    210                 215                 220
```

<210> SEQ ID NO 8
<211> LENGTH: 663
<212> TYPE: DNA
<213> ORGANISM: Deinococcus radiodurans

<400> SEQUENCE: 8

```
atgtcactcg cctcctacat cgaccacacg ctgcttaagg ccaccgccac gctcgccgac      60
```

```
atccgcacgc tgtgtgagga agcccgcgag cactcgttct acgcggtgtg catcaacccg    120
gtctttattc cccacgcccg cgcctggctc gaaggcagcg acgtgaaggt cgccaccgtc    180
tgcggctttc ccctcggcgc catcagctcc gagcagaaag ctctggaagc ccgcctgagc    240
gccgaaacgg cgccgacga aatcgatatg gtcatccaca tcggctcggc gcttgccggc    300
gactgggacg cggtggaagc cgacgtgcgg gcagtgcgcc gcgcggtgcc cgagcaggtg    360
ctcaaggtga ttatcgaaac ctgctacctg accgacgagc aaaagcgctt ggcgactgag    420
gtcgccgtac agggcggcgc cgacttcgtg aagacgagca caggcttcgg caccggcggc    480
gccaccgtgg acgacgtgcg cctgatggcg gaagtgatcg ggggccgcgc cggactcaag    540
gcggcgggcg cgtccgcac tcctgccgac gcgcaagcca tgatcgaggc gggcgcgacc    600
cggctgggca cctcgggcgg cgtgggtctg gtgtcgggcg cgaaaacgg agccggctac    660 tga                                                                 663

<210> SEQ ID NO 9
<211> LENGTH: 220
<212> TYPE: PRT
<213> ORGANISM: Deinococcus radiodurans

<400> SEQUENCE: 9

Met Ser Leu Ala Ser Tyr Ile Asp His Thr Leu Leu Lys Ala Thr Ala
1               5                   10                  15

Thr Leu Ala Asp Ile Arg Thr Leu Cys Glu Glu Ala Arg Glu His Ser
            20                  25                  30

Phe Tyr Ala Val Cys Ile Asn Pro Val Phe Ile Pro His Ala Arg Ala
        35                  40                  45

Trp Leu Glu Gly Ser Asp Val Lys Val Ala Thr Val Cys Gly Phe Pro
    50                  55                  60

Leu Gly Ala Ile Ser Ser Glu Gln Lys Ala Leu Glu Ala Arg Leu Ser
65                  70                  75                  80

Ala Glu Thr Gly Ala Asp Glu Ile Asp Met Val Ile His Ile Gly Ser
                85                  90                  95

Ala Leu Ala Gly Asp Trp Asp Ala Val Glu Ala Asp Val Arg Ala Val
            100                 105                 110

Arg Arg Ala Val Pro Glu Gln Val Leu Lys Val Ile Glu Thr Cys
        115                 120                 125

Tyr Leu Thr Asp Glu Gln Lys Arg Leu Ala Thr Glu Val Ala Val Gln
    130                 135                 140

Gly Gly Ala Asp Phe Val Lys Thr Ser Thr Gly Phe Gly Thr Gly Gly
145                 150                 155                 160

Ala Thr Val Asp Asp Val Arg Leu Met Ala Glu Val Ile Gly Gly Arg
                165                 170                 175

Ala Gly Leu Lys Ala Ala Gly Val Arg Thr Pro Ala Asp Ala Gln
            180                 185                 190

Ala Met Ile Glu Ala Gly Ala Thr Arg Leu Gly Thr Ser Gly Gly Val
        195                 200                 205

Gly Leu Val Ser Gly Gly Glu Asn Gly Ala Gly Tyr
    210                 215                 220

<210> SEQ ID NO 10
<211> LENGTH: 675
<212> TYPE: DNA
<213> ORGANISM: Propionibacterium acnes

<400> SEQUENCE: 10
```

```
atgtcctctg ccccactgtc tgccaccgag ttggccggca tgatcgatca caccctgctg        60
acccctgagg ccacccacaa cgacgtcgcc aagctggtcg ccgatgccaa aaaatatggg       120
acgtggtcgg tgtgcgtatc gccatcgatg ctgccgttga acctcgacat gggtgacgtg       180
catctggccg tcgtgtgcgg gtttccgtca ggcaagcaca ccagcgcagt aaaggctgct       240
gaggctcgtg aggccatcgc cgcaggggcc gaggaggtcg acatggtgat caaccttggt       300
ctggtaaagg agggacgctg ggaggacgtc accgccgata tcgctgccgt caagcaggcc       360
gtcccggatc cgaagatcct taaggtcatt atcgagtcgg cggtgctgac cgacgacgag       420
atcgtgcggg catgccaggc tgccgagaag gccggcgccg acttcgtcaa gacgtcgacg       480
ggattccacc cacgtggcgg cgcaagcgtc gaggccgtca aggtcatggc tgacactgtt       540
ggtggacgtc tgggcgtcaa agcgtccggc ggcatccgcg actaccagac ggcatgcgcg       600
atggtcgagg ccggggcgac gcgtctagga gtttcctcga ccgccaagat ccttgccgga       660
gctcccacgg agtga                                                       675
```

<210> SEQ ID NO 11
<211> LENGTH: 224
<212> TYPE: PRT
<213> ORGANISM: Propionibacterium acnes

<400> SEQUENCE: 11

```
Met Ser Ser Ala Pro Leu Ser Ala Thr Glu Leu Ala Gly Met Ile Asp
1               5                   10                  15

His Thr Leu Leu Thr Pro Glu Ala Thr His Asn Asp Val Ala Lys Leu
            20                  25                  30

Val Ala Asp Ala Lys Lys Tyr Gly Thr Trp Ser Val Cys Val Ser Pro
        35                  40                  45

Ser Met Leu Pro Leu Asn Leu Asp Met Gly Asp Val His Leu Ala Val
    50                  55                  60

Val Cys Gly Phe Pro Ser Gly Lys His Thr Ser Ala Val Lys Ala Ala
65                  70                  75                  80

Glu Ala Arg Glu Ala Ile Ala Ala Gly Ala Glu Glu Val Asp Met Val
                85                  90                  95

Ile Asn Leu Gly Leu Val Lys Glu Gly Arg Trp Glu Asp Val Thr Ala
            100                 105                 110

Asp Ile Ala Ala Val Lys Gln Ala Val Pro Asp Pro Lys Ile Leu Lys
        115                 120                 125

Val Ile Ile Glu Ser Ala Val Leu Thr Asp Asp Glu Ile Val Arg Ala
    130                 135                 140

Cys Gln Ala Ala Glu Lys Ala Gly Ala Asp Phe Val Lys Thr Ser Thr
145                 150                 155                 160

Gly Phe His Pro Arg Gly Gly Ala Ser Val Glu Ala Val Lys Val Met
                165                 170                 175

Ala Asp Thr Val Gly Gly Arg Leu Gly Val Lys Ala Ser Gly Gly Ile
            180                 185                 190

Arg Asp Tyr Gln Thr Ala Cys Ala Met Val Glu Ala Gly Ala Thr Arg
        195                 200                 205

Leu Gly Val Ser Ser Thr Ala Lys Ile Leu Ala Gly Ala Pro Thr Glu
    210                 215                 220
```

<210> SEQ ID NO 12
<211> LENGTH: 768
<212> TYPE: DNA
<213> ORGANISM: Chromobacterium violaceum

<400> SEQUENCE: 12

```
atgtctgcac tgattgaagc cgcgcgccgc gcgctgtccc tgatggacct gaccaccctc      60
aacgacgacg ataccgacga aaggtggcc gcgctgtgcc gcaaggccaa gagcccggac     120
ggcaccgtgg cggcggtatg cgtgtttccc cgcttcgtgc ccatcgccaa gaagacgctg    180
cgcgaagcgg gttgtccgga ggtgcaggtg gccaccgtca ccaacttccc gcacggcaat    240
gacgacgtct ccatcgcggt ggccgaaacc cgcgccgcca tcgcctacgg cgccgacgaa    300
gtggacgtgg tgttcccgta ccgcgcgctg atggccggca accgcgacat cggcttcgag    360
ctggtcaagg cctgcaagga agcctgcggc ggcaagctct tgaaagtgat catcgagagc    420
ggcgaactga aggacgcggc gctgatccgc gaagccagcg agatttccat ccgcgccggg    480
gccgacttca tcaagacttc caccggcaag gtgccggtca acgccacctt gcccgcggcc    540
gagaccatgc tggccgtgat caaggagcag ggcggccagt gcggcttcaa ggccgccggc    600
ggcgtcaaga gcgccaccga ggcggccgaa tacctggccc tggccgcgcg cctgctgggc    660
gaagattggg tgagcgcccg ccacttccgc ttcggcgcgt ccagcctgct ggccaatctg    720
cagatcgaga tcgccggcgg cgtcgccaag ccgagcagcg gctactga               768
```

<210> SEQ ID NO 13
<211> LENGTH: 255
<212> TYPE: PRT
<213> ORGANISM: Chromobacterium violaceum

<400> SEQUENCE: 13

```
Met Ser Ala Leu Ile Glu Ala Ala Arg Arg Ala Leu Ser Leu Met Asp
  1               5                  10                  15

Leu Thr Thr Leu Asn Asp Asp Thr Asp Glu Lys Val Ala Ala Leu
             20                  25                  30

Cys Arg Lys Ala Lys Ser Pro Asp Gly Thr Val Ala Ala Val Cys Val
         35                  40                  45

Phe Pro Arg Phe Val Pro Ile Ala Lys Lys Thr Leu Arg Glu Ala Gly
     50                  55                  60

Cys Pro Glu Val Gln Val Ala Thr Val Thr Asn Phe Pro His Gly Asn
 65                  70                  75                  80

Asp Asp Val Ser Ile Ala Val Ala Glu Thr Arg Ala Ala Ile Ala Tyr
                 85                  90                  95

Gly Ala Asp Glu Val Asp Val Val Phe Pro Tyr Arg Ala Leu Met Ala
            100                 105                 110

Gly Asn Arg Asp Ile Gly Phe Glu Leu Val Lys Ala Cys Lys Glu Ala
        115                 120                 125

Cys Gly Gly Lys Leu Leu Lys Val Ile Ile Glu Ser Gly Glu Leu Lys
    130                 135                 140

Asp Ala Ala Leu Ile Arg Glu Ala Ser Glu Ile Ser Ile Arg Ala Gly
145                 150                 155                 160

Ala Asp Phe Ile Lys Thr Ser Thr Gly Lys Val Pro Val Asn Ala Thr
                165                 170                 175

Leu Pro Ala Ala Glu Thr Met Leu Ala Val Ile Lys Glu Gln Gly Gly
            180                 185                 190

Gln Cys Gly Phe Lys Ala Ala Gly Gly Val Lys Ser Ala Thr Glu Ala
        195                 200                 205

Ala Glu Tyr Leu Ala Leu Ala Ala Arg Leu Leu Gly Glu Asp Trp Val
    210                 215                 220

Ser Ala Arg His Phe Arg Phe Gly Ala Ser Ser Leu Leu Ala Asn Leu
225                 230                 235                 240
```

Gln Ile Glu Ile Ala Gly Gly Val Ala Lys Pro Ser Ser Gly Tyr
            245                 250                 255

<210> SEQ ID NO 14
<211> LENGTH: 780
<212> TYPE: DNA
<213> ORGANISM: Agrobacterium tumefaciens

<400> SEQUENCE: 14

```
gtgaccatgg aactccagcg tccgcgcgaa gcggctgccc tcactttgtc cttgctggac      60
ctgaccaatc ttagggaaga ctgcacgccg cagcagatcg caaccctctg ccagcgggcg     120
catacggagt ttggcaacac cgctgccatt tgcatctggc cgcgtttcgt cgcgcaggcc     180
cgagcggcgt tcggaaaaga ccacacgatt cgcatcgcaa cggtcgtgaa tttcccctcc     240
ggcgatctcg atgtcgcgac cgtggttgcg gaaacggaag ctgcaatcgg cgatggcgcc     300
gacgaaatcg atctggtcat tccctatcgt aaattcatgg caggcgatga atcggcggtg     360
gccgaaatga tcgcggccgt gcgtaaggct tgcgcggcac ctgtgttgct caaggtcatt     420
cttgagaccg gtgagctgaa ggacaaggcc ctgatccgcc gtgcctcgga atcgccatt      480
gccgaagggg cggatttcat caagacctcg accggcaagg tcgccgtcaa tgccacgctg     540
gaagcggccg atatcatgct gcaggcgatc cgggacagca aaagaaggt gggcttcaag     600
ccggccggcg gcatcggcac ggtggaggac gcgacactat acctgcggct ggcggaaacc     660
atcatggcgc ccaactgggc catgccgtcg accttccgtt cggtgcctc gggcgtcctc     720
gatgatgtgc tgaacgtgct ggccggcggc gaaccggcca aggccgccag cgggtattga     780
```

<210> SEQ ID NO 15
<211> LENGTH: 259
<212> TYPE: PRT
<213> ORGANISM: Agrobacterium tumefaciens

<400> SEQUENCE: 15

Met Thr Met Glu Leu Gln Arg Pro Arg Glu Ala Ala Ala Leu Thr Leu
1               5                  10                  15

Ser Leu Leu Asp Leu Thr Asn Leu Arg Glu Asp Cys Thr Pro Gln Gln
            20                  25                  30

Ile Ala Thr Leu Cys Gln Arg Ala His Thr Glu Phe Gly Asn Thr Ala
        35                  40                  45

Ala Ile Cys Ile Trp Pro Arg Phe Val Ala Gln Ala Arg Ala Ala Phe
    50                  55                  60

Gly Lys Asp His Thr Ile Arg Ile Ala Thr Val Val Asn Phe Pro Ser
65                  70                  75                  80

Gly Asp Leu Asp Val Ala Thr Val Val Ala Glu Thr Glu Ala Ala Ile
                85                  90                  95

Gly Asp Gly Ala Asp Glu Ile Asp Leu Val Ile Pro Tyr Arg Lys Phe
            100                 105                 110

Met Ala Gly Asp Glu Ser Ala Val Ala Glu Met Ile Ala Ala Val Arg
        115                 120                 125

Lys Ala Cys Ala Ala Pro Val Leu Leu Lys Val Ile Leu Glu Thr Gly
    130                 135                 140

Glu Leu Lys Asp Lys Ala Leu Ile Arg Arg Ala Ser Glu Ile Ala Ile
145                 150                 155                 160

Ala Glu Gly Ala Asp Phe Ile Lys Thr Ser Thr Gly Lys Val Ala Val
                165                 170                 175

Asn Ala Thr Leu Glu Ala Ala Asp Ile Met Leu Gln Ala Ile Arg Asp

```
                180              185              190
Ser Lys Lys Val Gly Phe Lys Pro Ala Gly Ile Gly Thr Val
        195              200              205

Glu Asp Ala Thr Leu Tyr Leu Arg Leu Ala Glu Thr Ile Met Ala Pro
    210              215              220

Asn Trp Ala Met Pro Ser Thr Phe Arg Phe Gly Ala Ser Gly Val Leu
225              230              235              240

Asp Asp Val Leu Asn Val Leu Ala Gly Gly Pro Ala Lys Ala Ala
            245              250              255

Ser Gly Tyr

<210> SEQ ID NO 16
<211> LENGTH: 681
<212> TYPE: DNA
<213> ORGANISM: Anabaena variabilis

<400> SEQUENCE: 16
atggcagcag actatccgaa cattgatatt gcgccattta tcgatcacgc cctgttaacg      60
ccaacggcta ctccagagca ggttgaccaa tggtgtgaac aagcagacag atataatttt    120
gcgtcggttt gtttgtatcc tacttatgta aacaagcag cagaatttct ccacggcaag     180
aaacctaagg tttgtacggt aattggtttt cctactgggg ctacgactcg ctcagtcaag    240
ttgtatgagg cactggaagc ggtggagaat ggagccacag agctagatgt agtcatcaat    300
ttgggctgct tgaaatctgg taatacgaa gcagtacacc gggaaattgc cgaaatttgc     360
gaagagactg gacaagtagt taaagtaatt ttggaaacaa acttactgac ggatgcagaa    420
aaaaaaatcg cggccgatat agcaatggat gcaggagcca cattcttaaa accaatacag    480
ggttggaatg gcggtgctac agtggcagat gtgcggcttt taaagaaat cacacgggaa     540 agggtgggta taaaggcatc tggtgggatt cgcaccctca atcaagcct agacttaata    600 ttagcgggtg cgactagatt aggtacgtct cgtggtatcg atttaatcca ccagcgagat    660
aacccggaaa aagttgaata g                                               681

<210> SEQ ID NO 17
<211> LENGTH: 226
<212> TYPE: PRT
<213> ORGANISM: Anabaena variabilis

<400> SEQUENCE: 17

Met Ala Ala Asp Tyr Pro Asn Ile Asp Ile Ala Pro Phe Ile Asp His
1               5                  10                  15

Ala Leu Leu Thr Pro Thr Ala Thr Pro Glu Gln Val Asp Gln Trp Cys
            20                  25                  30

Glu Gln Ala Asp Arg Tyr Asn Phe Ala Ser Val Cys Leu Tyr Pro Thr
        35                  40                  45

Tyr Val Lys Gln Ala Ala Glu Phe Leu His Gly Lys Lys Pro Lys Val
    50                  55                  60

Cys Thr Val Ile Gly Phe Pro Thr Gly Ala Thr Thr Arg Ser Val Lys
65                  70                  75                  80

Leu Tyr Glu Ala Leu Glu Ala Val Glu Asn Gly Ala Thr Glu Leu Asp
                85                  90                  95

Val Val Ile Asn Leu Gly Cys Leu Lys Ser Gly Asn Thr Glu Ala Val
            100                 105                 110

His Arg Glu Ile Ala Glu Ile Cys Glu Glu Thr Gly Gln Val Val Lys
        115                 120                 125
```

```
Val Ile Leu Glu Thr Asn Leu Leu Thr Asp Ala Glu Lys Lys Ile Ala
            130                 135                 140

Ala Asp Ile Ala Met Asp Ala Gly Ala Thr Phe Leu Lys Thr Asn Thr
145                 150                 155                 160

Gly Trp Asn Gly Gly Ala Thr Val Ala Asp Val Arg Leu Leu Lys Glu
                165                 170                 175

Ile Thr Arg Glu Arg Val Gly Ile Lys Ala Ser Gly Gly Ile Arg Thr
            180                 185                 190

Leu Asn Gln Ala Leu Asp Leu Ile Leu Ala Gly Ala Thr Arg Leu Gly
        195                 200                 205

Thr Ser Arg Gly Ile Asp Leu Ile His Gln Arg Asp Asn Pro Glu Lys
    210                 215                 220

Val Glu
225

<210> SEQ ID NO 18
<211> LENGTH: 681
<212> TYPE: DNA
<213> ORGANISM: Pseudomonas syringae

<400> SEQUENCE: 18
atgaattcgc tcgaacccgc tgcactggcc caggccatcg atcacacctt gttggcggcg      60
gatgccagcc gagagcagat tgccacgctt tgcgcagaag cccgggaaca cggcttctac     120
tcggtgtgcg tgaactccag ccaggtgcct tttgccgccc gacaactggc cgggtctgcc     180
gtgaaggtct gtgcggtggt gggctttccg ctgggcgccg gctgagtgc cagcaaggcg     240 tcggaagcag ccctgacgat cgccgccggg gctcaggaaa tcgacatggt gctgaacatc     300
ggctggctca aggacggtct gttcgatgag gtccgcgacg atatcgccgc ggtgctgcaa     360
gcctgtggca aggtgccgct caaggtgatc ctggaaacct gcctgctcga tgaggcgcag     420
aaggtgcgcg cctgcgagat ctgccgcgag ctgggcgtgg cattcgtcaa gacctccact     480
ggcttcagcc gcagcggcgc gacgctcgag gatgtggcgc tgatgcgccg tgtggtaggc     540
cctgacatcg cgtcaaggc gtctggcggg gtgcgtgacg tggccacggc cagagcgatg     600
atcgaagctg gcgcaacgcg cctgggcacc agttccggga ttgcgatcgt gaccggcgca     660
ggtacggggg cgggttattg a                                               681

<210> SEQ ID NO 19
<211> LENGTH: 226
<212> TYPE: PRT
<213> ORGANISM: Pseudomonas syringae

<400> SEQUENCE: 19

Met Asn Ser Leu Glu Pro Ala Ala Leu Ala Gln Ala Ile Asp His Thr
1               5                   10                  15

Leu Leu Ala Ala Asp Ala Ser Arg Glu Gln Ile Ala Thr Leu Cys Ala
            20                  25                  30

Glu Ala Arg Glu His Gly Phe Tyr Ser Val Cys Val Asn Ser Ser Gln
        35                  40                  45

Val Pro Phe Ala Ala Arg Gln Leu Ala Gly Ser Ala Val Lys Val Cys
    50                  55                  60

Ala Val Val Gly Phe Pro Leu Gly Ala Gly Leu Ser Ala Ser Lys Ala
65                  70                  75                  80

Ser Glu Ala Ala Leu Thr Ile Ala Ala Gly Ala Gln Glu Ile Asp Met
                85                  90                  95

Val Leu Asn Ile Gly Trp Leu Lys Asp Gly Leu Phe Asp Glu Val Arg
```

```
            100                 105                 110

Asp Asp Ile Ala Ala Val Leu Gln Ala Cys Gly Lys Val Pro Leu Lys
        115                 120                 125

Val Ile Leu Glu Thr Cys Leu Leu Asp Glu Ala Gln Lys Val Arg Ala
    130                 135                 140

Cys Glu Ile Cys Arg Glu Leu Gly Val Ala Phe Val Lys Thr Ser Thr
145                 150                 155                 160

Gly Phe Ser Arg Ser Gly Ala Thr Leu Glu Asp Val Ala Leu Met Arg
                165                 170                 175

Arg Val Val Gly Pro Asp Ile Gly Val Lys Ala Ser Gly Gly Val Arg
            180                 185                 190

Asp Val Ala Thr Ala Arg Ala Met Ile Glu Ala Gly Ala Thr Arg Leu
        195                 200                 205

Gly Thr Ser Ser Gly Ile Ala Ile Val Thr Gly Ala Gly Thr Gly Ala
    210                 215                 220

Gly Tyr
225

<210> SEQ ID NO 20
<211> LENGTH: 669
<212> TYPE: DNA
<213> ORGANISM: Erwinia carotovora

<400> SEQUENCE: 20
atgactgact acgcacgcta tatcgaccac accctgctgg cagcaaatgc caccgaacag      60
caaatcgtca cgctgtgcga tgaagcgata gcgcaccatt tttatgccgt ctgtgttaat     120
tccggctacg ttcccttagt agctgaaaaa ttgaaaggtt cagcggtaca ggtgtgctcg     180
gttattggat ttcctctcgg tgcaggcctg acttccagca aagcatttga agcgaaagcc     240
gcgattgatg ccggtgcaca ggaaatcgac atggtgatta acgtcggctg gctgaaaagc     300
gggaagattg atgccgtcaa agcggatatt caggccgtgc gtggggtttg cgccgctata     360
ccgttgaagg taatattgga aacctgtctg cttgatgacg aacagattgt gctggtgtgt     420
gaaatgtgtc gtcagttgga tgtcgcgttc gtcaaaacgt ctaccggttt cagcaccgac     480
ggcgcacgcg aagaacacgt tcgactgatg cgtagcactg tcggcagcga gatgggtgta     540
aaagcctccg gcgcggttcg cgatcgcgaa acggcacaac gaatgattga agcaggcgcc     600
acgcgtattg gcaccagttc aggcgttgct atcgtttctg atgacgctgc cgcagcaggg     660
aactactaa                                                             669

<210> SEQ ID NO 21
<211> LENGTH: 222
<212> TYPE: PRT
<213> ORGANISM: Erwinia carotovora

<400> SEQUENCE: 21

Met Thr Asp Tyr Ala Arg Tyr Ile Asp His Thr Leu Leu Ala Ala Asn
1               5                   10                  15

Ala Thr Glu Gln Gln Ile Val Thr Leu Cys Asp Glu Ala Ile Ala His
            20                  25                  30

His Phe Tyr Ala Val Cys Val Asn Ser Gly Tyr Val Pro Leu Val Ala
        35                  40                  45

Glu Lys Leu Lys Gly Ser Ala Val Gln Val Cys Ser Val Ile Gly Phe
    50                  55                  60

Pro Leu Gly Ala Gly Leu Thr Ser Ser Lys Ala Phe Glu Ala Lys Ala
65                  70                  75                  80
```

```
Ala Ile Asp Ala Gly Ala Gln Glu Ile Asp Met Val Ile Asn Val Gly
            85                  90                  95

Trp Leu Lys Ser Gly Lys Ile Asp Ala Val Lys Ala Asp Ile Gln Ala
            100                 105                 110

Val Arg Gly Val Cys Ala Ala Ile Pro Leu Lys Val Ile Leu Glu Thr
            115                 120                 125

Cys Leu Asp Asp Glu Gln Ile Val Leu Val Cys Glu Met Cys Arg
130                 135                 140

Gln Leu Asp Val Ala Phe Val Lys Thr Ser Thr Gly Phe Ser Thr Asp
145                 150                 155                 160

Gly Ala Arg Glu Glu His Val Arg Leu Met Arg Ser Thr Val Gly Ser
            165                 170                 175

Glu Met Gly Val Lys Ala Ser Gly Ala Val Arg Asp Arg Glu Thr Ala
            180                 185                 190

Gln Arg Met Ile Glu Ala Gly Ala Thr Arg Ile Gly Thr Ser Ser Gly
            195                 200                 205

Val Ala Ile Val Ser Asp Asp Ala Ala Ala Gly Asn Tyr
210                 215                 220
```

<210> SEQ ID NO 22
<211> LENGTH: 684
<212> TYPE: DNA
<213> ORGANISM: Desulfotalea psychrophila

<400> SEQUENCE: 22

```
atgaatacaa tcattagccc gaaagaaatt gccttgtata ttgatcacac tctcctcaaa     60
cctgaggcaa gccctgcagc tattcgtacc ctatgcgcag aagctcgtga gtactctttc    120
aagactgtat gcgtcaactc ttgctatgtc cctctctgtg tggaagaact tcaagcttgc    180
ccgttgatg tttgctcggt ggtgggttc ccacttgggg ctatgctgag ttcggcaaag     240
gcctacgagg caaaacttgc agtggcagcc ggggccgacg aaattgatat ggttatcaat    300
attggtctct tgaaggcagg agaacttgaa gctgttcggg cagatattga aacagttttt    360
gccgcctgtg gagaggcaga ccttaaggtg atcattgaga caggcctgct cagcgatgcg    420
gagaaaaaaa gcgtctgtca gatatgcaag gaagttggtg tcgcctttgt taagacctcc    480
acgggttttg tcatggtgg cgcaaccgtt gccgatgtag aacttatgcg tgctgttgtt    540
ggtgagagat gtaaggttaa ggcctctggc ggggtacgca accttgccga tgcccgcgcc    600
ctgatagcgg caggagccaa tagaattggg gcaagtgccg tatcgcaatg tgtcaatgga    660
gaagaggtcc cccttctcg ttaa                                           684
```

<210> SEQ ID NO 23
<211> LENGTH: 227
<212> TYPE: PRT
<213> ORGANISM: Desulfotalea psychrophila

<400> SEQUENCE: 23

```
Met Asn Thr Ile Ile Ser Pro Lys Glu Ile Ala Leu Tyr Ile Asp His
1               5                   10                  15

Thr Leu Leu Lys Pro Glu Ala Ser Pro Ala Ala Ile Arg Thr Leu Cys
            20                  25                  30

Ala Glu Ala Arg Glu Tyr Ser Phe Lys Thr Val Cys Val Asn Ser Cys
        35                  40                  45

Tyr Val Pro Leu Cys Val Glu Glu Leu Gln Ala Cys Pro Val Asp Val
50                  55                  60
```

```
Cys Ser Val Val Gly Phe Pro Leu Gly Ala Met Leu Ser Ser Ala Lys
 65                  70                  75                  80

Ala Tyr Glu Ala Lys Leu Ala Val Ala Ala Gly Ala Asp Glu Ile Asp
                 85                  90                  95

Met Val Ile Asn Ile Gly Leu Leu Lys Ala Gly Glu Leu Glu Ala Val
            100                 105                 110

Arg Ala Asp Ile Glu Thr Val Phe Ala Ala Cys Gly Glu Ala Asp Leu
        115                 120                 125

Lys Val Ile Ile Glu Thr Gly Leu Leu Ser Asp Ala Glu Lys Lys Ser
    130                 135                 140

Val Cys Gln Ile Cys Lys Glu Val Gly Val Ala Phe Val Lys Thr Ser
145                 150                 155                 160

Thr Gly Phe Gly His Gly Gly Ala Thr Val Ala Asp Val Glu Leu Met
                165                 170                 175

Arg Ala Val Val Gly Glu Arg Cys Lys Val Lys Ala Ser Gly Gly Val
            180                 185                 190

Arg Asn Leu Ala Asp Ala Arg Ala Leu Ile Ala Ala Gly Ala Asn Arg
        195                 200                 205

Ile Gly Ala Ser Ala Gly Ile Ala Ile Val Asn Gly Glu Glu Val Pro
    210                 215                 220

Pro Ser Arg
225

<210> SEQ ID NO 24
<211> LENGTH: 636
<212> TYPE: DNA
<213> ORGANISM: Bacillus subtilis

<400> SEQUENCE: 24
atgtcattag ccaacataat tgatcataca gctttgaaac cgcatacaca aaaagcggac      60
attctaaaac taattgaaga agcgaaaaca tacaaatttg cttcagtatg tgtcaatccg     120
acatgggtgg agcttgctgc aaaagagctt aagggaactg gagtcgacgt tgtacggtc     180 atcggcttcc cgctcggtgc caatacaact gaaacaaaag cgttcgaaac aaaagacgcc     240
atttcaaaag gcgccactga agtggatatg gtcattaata ttgccgcttt aaaagacaag     300
gaagacgatg tggtggaagc tgatatccgc ggtgtagtgg aagctgtagc cggaaaagcg     360
cttgtcaaag tcattatcga aacgtgcctt ctgactgatg aagaaaaaga acgtgcatgc     420
cgtttagcgg tgtctgcggg agcggatttc gtaaaaacat caacaggctt ttctacaggc     480
ggcgcaacga aggaagatat cgccttaatg cgcaaaacag tagggcctga tatcggcgtg     540
aaagcatctg gcggcgtcag aacgaaagaa gatgtagaca caatggtaga ggccggagca     600
agccgaattg cgccagcgca ggcgtttcta tcgtaa                              636

<210> SEQ ID NO 25
<211> LENGTH: 211
<212> TYPE: PRT
<213> ORGANISM: Bacillus subtilis

<400> SEQUENCE: 25

Met Ser Leu Ala Asn Ile Ile Asp His Thr Ala Leu Lys Pro His Thr
  1               5                  10                  15

Gln Lys Ala Asp Ile Leu Lys Leu Ile Glu Glu Ala Lys Thr Tyr Lys
                 20                  25                  30

Phe Ala Ser Val Cys Val Asn Pro Thr Trp Val Glu Leu Ala Ala Lys
             35                  40                  45
```

```
Glu Leu Lys Gly Thr Gly Val Asp Val Cys Thr Val Ile Gly Phe Pro
     50                  55                  60
Leu Gly Ala Asn Thr Thr Glu Thr Lys Ala Phe Glu Thr Lys Asp Ala
 65                  70                  75                  80
Ile Ser Lys Gly Ala Thr Glu Val Asp Met Val Ile Asn Ile Ala Ala
                 85                  90                  95
Leu Lys Asp Lys Glu Asp Val Val Glu Ala Asp Ile Arg Gly Val
                100                 105                 110
Val Glu Ala Val Ala Gly Lys Ala Leu Val Lys Val Ile Glu Thr
            115                 120                 125
Cys Leu Leu Thr Asp Glu Glu Lys Glu Arg Ala Cys Arg Leu Ala Val
130                 135                 140
Ser Ala Gly Ala Asp Phe Val Lys Thr Ser Thr Gly Phe Ser Thr Gly
145                 150                 155                 160
Gly Ala Thr Lys Glu Asp Ile Ala Leu Met Arg Lys Thr Val Gly Pro
                165                 170                 175
Asp Ile Gly Val Lys Ala Ser Gly Gly Val Arg Thr Lys Glu Asp Val
                180                 185                 190
Asp Thr Met Val Glu Ala Gly Ala Ser Arg Ile Ala Pro Ala Gln Ala
            195                 200                 205
Phe Leu Ser
    210

<210> SEQ ID NO 26
<211> LENGTH: 672
<212> TYPE: DNA
<213> ORGANISM: Listeria innocua

<400> SEQUENCE: 26
atgacaattg ccaaaatgat cgaccacact gctttaaaac cagacacaac gaaagaacaa      60
attttaacat taacaaaaga agcaagagaa tatggttttg cttccgtatg cgtgaatcca     120
acttgggtga aattatccgc tgaacagctt tcaggagcag aatccgttgt atgtacagtt     180
atcggtttcc cacttggagc aaatacacca gaagtaaaag cttttgaagt gaaaaatgcc     240
atcgaaaacg gcgctaaaga agtggatatg gttattaata tcggcgcatt aaaagacaaa     300
gacgatgaat agtagaacg tgatattcgt gctgtagttg atgctgccaa agggaaagca     360
ttagtaaaag taattattga acttgccta ttaacagacg aagaaaaagt tcgcgcatgt     420
gaaatcgctg taaaagcagg aacagacttc gttaaaacat ccactggatt ctccacaggt     480
ggcgcaactg ccgaagatat tgctttaatg cgtaaaactg taggaccaaa catcggcgta     540
aaagcatctg gcggagttcg tacaaaagaa gacgtagaaa aatgattga agcaggtgca     600 actcgtatcg gcgcaagtgc aggtgtcgca attgtttccg gcgaaaaacc agctaaacca     660
gataattact aa                                                         672

<210> SEQ ID NO 27
<211> LENGTH: 223
<212> TYPE: PRT
<213> ORGANISM: Listeria innocua

<400> SEQUENCE: 27

Met Thr Ile Ala Lys Met Ile Asp His Thr Ala Leu Lys Pro Asp Thr
  1               5                  10                  15
Thr Lys Glu Gln Ile Leu Thr Leu Thr Lys Glu Ala Arg Glu Tyr Gly
             20                  25                  30
Phe Ala Ser Val Cys Val Asn Pro Thr Trp Val Lys Leu Ser Ala Glu
```

```
                35                  40                  45
Gln Leu Ser Gly Ala Glu Ser Val Val Cys Thr Val Ile Gly Phe Pro
         50                  55                  60
Leu Gly Ala Asn Thr Pro Glu Val Lys Ala Phe Glu Val Lys Asn Ala
 65                  70                  75                  80
Ile Glu Asn Gly Ala Lys Glu Val Asp Met Val Ile Asn Ile Gly Ala
                 85                  90                  95
Leu Lys Asp Lys Asp Asp Glu Leu Val Glu Arg Asp Ile Arg Ala Val
            100                 105                 110
Val Asp Ala Ala Lys Gly Lys Ala Leu Val Lys Val Ile Glu Thr
            115                 120                 125
Cys Leu Leu Thr Asp Glu Glu Lys Val Arg Ala Cys Glu Ile Ala Val
            130                 135                 140
Lys Ala Gly Thr Asp Phe Val Lys Thr Ser Thr Gly Phe Ser Thr Gly
145                 150                 155                 160
Gly Ala Thr Ala Glu Asp Ile Ala Leu Met Arg Lys Thr Val Gly Pro
                165                 170                 175
Asn Ile Gly Val Lys Ala Ser Gly Gly Val Arg Thr Lys Glu Asp Val
            180                 185                 190
Glu Lys Met Ile Glu Ala Gly Ala Thr Arg Ile Gly Ala Ser Ala Gly
            195                 200                 205
Val Ala Ile Val Ser Gly Glu Lys Pro Ala Lys Pro Asp Asn Tyr
    210                 215                 220

<210> SEQ ID NO 28
<211> LENGTH: 648
<212> TYPE: DNA
<213> ORGANISM: Clostridium acetobutylicum

<400> SEQUENCE: 28
atgaatattg ctaaaattat agatcataca gcattaaagc cagatacaac aaaggagcag    60
atactaaaac taatagaaga agctaaacaa ataactttg catcagtttg tgtaaatcca   120
aagtgggtta agaggcaag ctgtgcatta aaggacagca gtgttaaagt gtgtactgta   180
atagggtttc ctcttggagc taatacaact gctacaaaag tatttgaaac acaagatgct   240
attaaaaatg gtgcagaaga agtagatatg gttgtttcta taggagaatt aaaagataaa   300
aatgatgatt atgtagaaaa agatatagaa gaagttgtta aggcagctag tggaaaggcc   360
ttagttaaag taattattga aacttgtctt cttaccgaag aagagaagat aagagcgtgt   420
aaactagcta aaaagcagg tgcagatttt gttaaaacat caacagggtt ttcaacagga   480
ggggctaagg cagaagatat taaattaatg agaaaaacag ttggagctgg tatgggagtt   540
aaggcctcag gtggtattca tacaagagaa gaagcaatta aacttataga agctggagct   600
acacgtattg gagctagtgc aagtatagat ataatttcag aaaattaa               648

<210> SEQ ID NO 29
<211> LENGTH: 215
<212> TYPE: PRT
<213> ORGANISM: Clostridium acetobutylicum

<400> SEQUENCE: 29

Met Asn Ile Ala Lys Ile Ile Asp His Thr Ala Leu Lys Pro Asp Thr
  1               5                  10                  15
Thr Lys Glu Gln Ile Leu Lys Leu Ile Glu Glu Ala Lys Gln Asn Asn
            20                  25                  30
Phe Ala Ser Val Cys Val Asn Pro Lys Trp Val Lys Glu Ala Ser Cys
```

```
                35                  40                  45
Ala Leu Lys Asp Ser Ser Val Lys Val Cys Thr Val Ile Gly Phe Pro
 50                  55                  60
Leu Gly Ala Asn Thr Thr Ala Thr Lys Val Phe Glu Thr Gln Asp Ala
 65                  70                  75                  80
Ile Lys Asn Gly Ala Glu Val Asp Met Val Val Ser Ile Gly Glu
                 85                  90                  95
Leu Lys Asp Lys Asn Asp Asp Tyr Val Glu Lys Asp Ile Glu Val
                100                 105                 110
Val Lys Ala Ala Ser Gly Lys Ala Leu Val Lys Val Ile Glu Thr
                115                 120                 125
Cys Leu Leu Thr Glu Glu Lys Ile Arg Ala Cys Lys Leu Ala Lys
    130                 135                 140
Lys Ala Gly Ala Asp Phe Val Lys Thr Ser Thr Gly Phe Ser Thr Gly
145                 150                 155                 160
Gly Ala Lys Ala Glu Asp Ile Lys Leu Met Arg Lys Thr Val Gly Ala
                165                 170                 175
Gly Met Gly Val Lys Ala Ser Gly Gly Ile His Thr Arg Glu Glu Ala
                180                 185                 190
Ile Lys Leu Ile Glu Ala Gly Ala Thr Arg Ile Gly Ala Ser Ala Ser
                195                 200                 205
Ile Asp Ile Ile Ser Glu Asn
    210                 215

<210> SEQ ID NO 30
<211> LENGTH: 822
<212> TYPE: DNA
<213> ORGANISM: Geobacillus kaustophilus

<400> SEQUENCE: 30
atggagctca taacccagcc tagttgctgg gttttttctg tcttttttccg gagacaatac     60
ggatggctag ttttttgtcga gggagcatgg tatgatggta gacgtcagac tttccatctt    120
gacggaaatg gcagaaaggg gtttctccga atgacgatga atatcgcgaa atgatcgat     180
catacgctgc tcaaaccgga agcgacagaa caacaaatcg tgcaactgtg cacggaagca    240
aagcaatacg gctttgcttc cgtgtgcgtc aacccaacgt gggtgaaaac ggcggcgcgc    300
gagctttccg gcacggatgt ccgcgtctgc acggtcatcg gctttccact ggggcaacg    360
acgccggaaa caaggcgtt tgaaacaacg aacgccatcg aaacggcgc tcgcgaagtc    420
gacatggtga tcaacatcgg cgcgttaaaa agcgggcaag acgagcttgt cgagcgcgac    480
attcgtgcgg ttgtcgaagc ggcggctggc agggcgcttg tcaaagtgat cgttgaaacg    540
gcgcttttga ccgatgagga aaaagtgcgc gcctgccagc tcgcagtgaa agccggcgct    600
gattatgtga aaacgtcgac cgggtttttcc ggcggaggtg cgacggtgga ggatgtggcg    660
ttgatgcgga aaacggtcgg cgacagagca ggcgtcaaag catcaggcgg cgtccgtgac    720
tggaaaaccg ctgaggcgat gatcaacgcc ggcgcgacgc gcatcggcac aagctctggg    780
gtggcgatcg tcaccggcgg gacgggccgc gctgactact aa                        822

<210> SEQ ID NO 31
<211> LENGTH: 273
<212> TYPE: PRT
<213> ORGANISM: Geobacillus kaustophilus

<400> SEQUENCE: 31

Met Glu Leu Ile Thr Gln Pro Ser Cys Trp Val Phe Ser Val Phe Phe
```

```
              1               5              10              15
Arg Arg Gln Tyr Gly Trp Leu Val Phe Val Glu Gly Ala Trp Tyr Asp
                    20                  25                  30

Gly Arg Arg Gln Thr Phe His Leu Asp Gly Asn Gly Arg Lys Gly Phe
                35                  40                  45

Leu Arg Met Thr Met Asn Ile Ala Lys Met Ile Asp His Thr Leu Leu
 50                  55                  60

Lys Pro Glu Ala Thr Glu Gln Gln Ile Val Gln Leu Cys Thr Glu Ala
 65                  70                  75                  80

Lys Gln Tyr Gly Phe Ala Ser Val Cys Val Asn Pro Thr Trp Val Lys
                    85                  90                  95

Thr Ala Ala Arg Glu Leu Ser Gly Thr Asp Val Arg Val Cys Thr Val
                100                 105                 110

Ile Gly Phe Pro Leu Gly Ala Thr Thr Pro Glu Thr Lys Ala Phe Glu
                115                 120                 125

Thr Thr Asn Ala Ile Glu Asn Gly Ala Arg Glu Val Asp Met Val Ile
                130                 135                 140

Asn Ile Gly Ala Leu Lys Ser Gly Gln Asp Glu Leu Val Glu Arg Asp
145                 150                 155                 160

Ile Arg Ala Val Val Glu Ala Ala Gly Arg Ala Leu Val Lys Val
                    165                 170                 175

Ile Val Glu Thr Ala Leu Leu Thr Asp Glu Glu Lys Val Arg Ala Cys
                180                 185                 190

Gln Leu Ala Val Lys Ala Gly Ala Asp Tyr Val Lys Thr Ser Thr Gly
                195                 200                 205

Phe Ser Gly Gly Gly Ala Thr Val Glu Asp Val Ala Leu Met Arg Lys
                210                 215                 220

Thr Val Gly Asp Arg Ala Gly Val Lys Ala Ser Gly Gly Val Arg Asp
225                 230                 235                 240

Trp Lys Thr Ala Glu Ala Met Ile Asn Ala Gly Ala Thr Arg Ile Gly
                    245                 250                 255

Thr Ser Ser Gly Val Ala Ile Val Thr Gly Gly Thr Gly Arg Ala Asp
                260                 265                 270

Tyr

<210> SEQ ID NO 32
<211> LENGTH: 675
<212> TYPE: DNA
<213> ORGANISM: Bacillus halodurans

<400> SEQUENCE: 32
atgtcacgtt cgattgcaca atgattgat catacgctac ttaaaccaaa tacaacagaa      60
gaccaaattg taaagctctg tgaggaagca aggaatatt catttgcatc tgtttgtgtg     120
aatcctactt gggtcgctct tgctgcgcag ttgctaaaag atgcacctga tgtgaaagta     180
tgtacagtta tcggctttcc gttaggggca acgactccgg aagtgaaagc gtttgaaacg     240
actaatgcca ttgaaaatgg agcgacagaa gtggacatgg tcattaacat tggagcgtta     300
aaagataaac aatacgagct tgttggacgc gacattcaag cggttgttaa agcagcagaa     360
gggaaagcat taacgaaagt aatcattgaa acatcgttat aacggagga agagaagaag     420 gctgcgtgtg agcttgccgt aaaagcagga gccgactttg tcaaaacgtc gactggattc     480
tctggcggag gtgctacggc tgaggatatc gcgctcatgc gaaagtggt cggaccaaat     540 ttaggagtca aagcttctgg aggtgttaga gatctgtccg acgcgaaagc gatgattgat     600
```

```
gctggtgcta ctcggattgg tgcgagtgct ggggtggcga ttgttaacgg ggagcgtagc    660
gaagggagtt attaa                                                    675

<210> SEQ ID NO 33
<211> LENGTH: 224
<212> TYPE: PRT
<213> ORGANISM: Bacillus halodurans

<400> SEQUENCE: 33

Met Ser Arg Ser Ile Ala Gln Met Ile Asp His Thr Leu Leu Lys Pro
1               5                  10                  15

Asn Thr Thr Glu Asp Gln Ile Val Lys Leu Cys Glu Glu Ala Lys Glu
            20                  25                  30

Tyr Ser Phe Ala Ser Val Cys Val Asn Pro Thr Trp Val Ala Leu Ala
        35                  40                  45

Ala Gln Leu Leu Lys Asp Ala Pro Asp Val Lys Val Cys Thr Val Ile
    50                  55                  60

Gly Phe Pro Leu Gly Ala Thr Thr Pro Glu Val Lys Ala Phe Glu Thr
65                  70                  75                  80

Thr Asn Ala Ile Glu Asn Gly Ala Thr Glu Val Asp Met Val Ile Asn
                85                  90                  95

Ile Gly Ala Leu Lys Asp Lys Gln Tyr Glu Leu Val Gly Arg Asp Ile
            100                 105                 110

Gln Ala Val Val Lys Ala Glu Gly Lys Ala Leu Thr Lys Val Ile
        115                 120                 125

Ile Glu Thr Ser Leu Leu Thr Glu Glu Leu Lys Lys Ala Ala Cys Glu
    130                 135                 140

Leu Ala Val Lys Ala Gly Ala Asp Phe Val Lys Thr Ser Thr Gly Phe
145                 150                 155                 160

Ser Gly Gly Gly Ala Thr Ala Glu Asp Ile Ala Leu Met Arg Lys Val
                165                 170                 175

Val Gly Pro Asn Leu Gly Val Lys Ala Ser Gly Gly Val Arg Asp Leu
            180                 185                 190

Ser Asp Ala Lys Ala Met Ile Asp Ala Gly Ala Thr Arg Ile Gly Ala
        195                 200                 205

Ser Ala Gly Val Ala Ile Val Asn Gly Glu Arg Ser Glu Gly Ser Tyr
    210                 215                 220

<210> SEQ ID NO 34
<211> LENGTH: 672
<212> TYPE: DNA
<213> ORGANISM: Bacillus licheniformis

<400> SEQUENCE: 34
atgacaaaac aaattgcgcg aatgatcgat cacactgcat tgaagccaga taccgtcaaa    60
tccgaaatcg aagcgctttg caaagaagcg cgtgtttacg ttttgcctc cgtttgtgtc    120 aacccttgct gggtgaagct tgcgccgag cttcttaaag agtcagaggt gaaagtatgt    180
acagttatcg ctttcctttt aggtgcagcg tctccggaaa caaagccctt gaaaccagg    240 caggcaattg cagacggtgc cggtgaagtt gatatggtga tcaacatcgg tgcactaaaa    300
gaccgcgata cgggaacagt ggaacatgac atcaggcgg tgcagacgc ggccgacggc    360 aaagctcttg taaagtcat catagagacg tcgcttttga cggatgaaga aaaaaggctg    420
gcttgtgaac tggccgtaaa agcaggcgcc gactttgtca aaacatcgac cggttttcc    480 ggcggcggtg cgacagtccg ggatataaaa ctgatgcggg aagctgtcgg acctgatatc    540
```

```
ggcgttaaag cttcaggtgg cgtccgcgat aaggaaagcg cacttgccat gattgaagcc    600
ggagcgacga gaatcggagc gagcgccggc gtgtcgattg tcaaagggtt aacagcggat    660
gaagactact aa                                                        672
```

<210> SEQ ID NO 35
<211> LENGTH: 223
<212> TYPE: PRT
<213> ORGANISM: Bacillus licheniformis

<400> SEQUENCE: 35

```
Met Thr Lys Gln Ile Ala Arg Met Ile Asp His Thr Ala Leu Lys Pro
1               5                   10                  15

Asp Thr Val Lys Ser Glu Ile Glu Ala Leu Cys Lys Glu Ala Arg Val
            20                  25                  30

Tyr Gly Phe Ala Ser Val Cys Val Asn Pro Cys Trp Val Lys Leu Cys
        35                  40                  45

Ala Glu Leu Leu Lys Glu Ser Glu Val Lys Val Cys Thr Val Ile Gly
    50                  55                  60

Phe Pro Leu Gly Ala Ala Ser Pro Glu Thr Lys Ala Phe Glu Thr Arg
65                  70                  75                  80

Gln Ala Ile Ala Asp Gly Ala Gly Glu Val Asp Met Val Ile Asn Ile
                85                  90                  95

Gly Ala Leu Lys Asp Arg Asp Thr Gly Thr Val Glu His Asp Ile Arg
            100                 105                 110

Ala Val Thr Asp Ala Ala Asp Gly Lys Ala Leu Val Lys Val Ile Ile
        115                 120                 125

Glu Thr Ser Leu Leu Thr Asp Glu Glu Lys Arg Leu Ala Cys Glu Leu
    130                 135                 140

Ala Val Lys Ala Gly Ala Asp Phe Val Lys Thr Ser Thr Gly Phe Ser
145                 150                 155                 160

Gly Gly Gly Ala Thr Val Arg Asp Ile Lys Leu Met Arg Glu Ala Val
                165                 170                 175

Gly Pro Asp Ile Gly Val Lys Ala Ser Gly Gly Val Arg Asp Lys Glu
            180                 185                 190

Ser Ala Leu Ala Met Ile Glu Ala Gly Ala Thr Arg Ile Gly Ala Ser
        195                 200                 205

Ala Gly Val Ser Ile Val Lys Gly Leu Thr Ala Asp Glu Asp Tyr
    210                 215                 220
```

<210> SEQ ID NO 36
<211> LENGTH: 663
<212> TYPE: DNA
<213> ORGANISM: Streptococcus mutans

<400> SEQUENCE: 36

```
atgaaaatca atcaatatat tgaccatact ttattaaaac cagaaagtag gcaagatcag    60
attgataaac tgattcgaga agctaagaca tataattttg ccagtgtctg tatcaatcca    120
acttgggttt cttatgcggc taaagctctt gaaggaacag acattaaagt ttgtactgtt    180
attggttttc ctttaggagc aacgactagt gctgtaaaag ccttttgaaac caaggatgct    240 attagtcatg gagctgacga agttgatatg gttatcaata ttggtcaagc taaatctggt    300
cattttgctt ttgttgaaga agatattcgg gcagttgttg aagccagtgg tgacaaattg    360
gtgaaagtta ttattgaaac ttgtctcctt acagataaag aaaaaattaa agcttgtcaa    420
gctgcagtag cagcaggtgc tgatttcgtt aaaacatcaa ctggttttc aactgctgga    480
```

```
gctaggttag atgatgttcg tcttatgcgt caaacggtag gacctgatgt tggagtaaag      540
gcggcaggag gaacgcgatc tttagaagat gcgcaagctt ttattgaagc aggtgcaaca      600
cgtattggga catctgctgg agttactatt atggaaggaa agcaaacaaa cagtggttat      660
tga                                                                    663
```

```
<210> SEQ ID NO 37
<211> LENGTH: 220
<212> TYPE: PRT
<213> ORGANISM: Streptococcus mutans

<400> SEQUENCE: 37

Met Lys Ile Asn Gln Tyr Ile Asp His Thr Leu Leu Lys Pro Glu Ser
1               5                   10                  15

Arg Gln Asp Gln Ile Asp Lys Leu Ile Arg Glu Ala Lys Thr Tyr Asn
            20                  25                  30

Phe Ala Ser Val Cys Ile Asn Pro Thr Trp Val Ser Tyr Ala Ala Lys
        35                  40                  45

Ala Leu Glu Gly Thr Asp Ile Lys Val Cys Thr Val Ile Gly Phe Pro
    50                  55                  60

Leu Gly Ala Thr Thr Ser Ala Val Lys Ala Phe Glu Thr Lys Asp Ala
65                  70                  75                  80

Ile Ser His Gly Ala Asp Glu Val Asp Met Val Ile Asn Ile Gly Gln
                85                  90                  95

Ala Lys Ser Gly His Phe Ala Phe Val Glu Glu Asp Ile Arg Ala Val
            100                 105                 110

Val Glu Ala Ser Gly Asp Lys Leu Val Lys Val Ile Glu Thr Cys
        115                 120                 125

Leu Leu Thr Asp Lys Glu Lys Ile Lys Ala Cys Gln Ala Ala Val Ala
    130                 135                 140

Ala Gly Ala Asp Phe Val Lys Thr Ser Thr Gly Phe Ser Thr Ala Gly
145                 150                 155                 160

Ala Arg Leu Asp Asp Val Arg Leu Met Arg Gln Thr Val Gly Pro Asp
                165                 170                 175

Val Gly Val Lys Ala Ala Gly Gly Thr Arg Ser Leu Glu Asp Ala Gln
            180                 185                 190

Ala Phe Ile Glu Ala Gly Ala Thr Arg Ile Gly Thr Ser Ala Gly Val
        195                 200                 205

Thr Ile Met Glu Gly Lys Gln Thr Asn Ser Gly Tyr
    210                 215                 220
```

```
<210> SEQ ID NO 38
<211> LENGTH: 663
<212> TYPE: DNA
<213> ORGANISM: Staphylococcus epidermidis

<400> SEQUENCE: 38
atgaataaag caaaattgat agaccataca ttattaaaac ctgattcaac aaaggaacaa       60
atagatacta ttataaatga agcaaaagca tatcagttta gtctgtatg tgtgaaccct      120 acacatgtac aatatgcatc tgaacaactt aaaggaacag acgttttagt gtgtactgtt      180
attggatttc cactaggtgc aacaactaca gcggttaaat cttatgaaac aaaagatgcg      240
attaacaatg gtgcccaaga gattgatatg gtgataaata ttggagcact taaggatggc      300
cgttttgatg aagtgcaaaa tgatatcgaa gccgtcgttc aagcagccaa tggtaaaaca      360
gttaaggtaa ttattgagac tgtttttatta actgagaaag agaagattaa agcatgtcaa      420
```

```
ttatctgaag cggcaggtgc acattttgtt aaaacatcca caggttttgc tggtgggggt    480
gcaacagttg aagatgtaaa attaatgaaa gatactgttg gtgatcgttt agaagtaaaa    540
gcgtcaggcg gcgtgagaaa tctagaagat tttaataata tgattgaagc gggtgctaca    600
cgtattggtg ctagtgccgg tgtgcaaatt attcaaggac ttgaatcaaa tactgattac    660
taa                                                                 663
```

```
<210> SEQ ID NO 39
<211> LENGTH: 220
<212> TYPE: PRT
<213> ORGANISM: Staphylococcus epidermidis

<400> SEQUENCE: 39
```

```
Met Asn Lys Ala Lys Leu Ile Asp His Thr Leu Leu Lys Pro Asp Ser
  1               5                  10                  15

Thr Lys Glu Gln Ile Asp Thr Ile Ile Asn Glu Ala Lys Ala Tyr Gln
             20                  25                  30

Phe Lys Ser Val Cys Val Asn Pro Thr His Val Gln Tyr Ala Ser Glu
         35                  40                  45

Gln Leu Lys Gly Thr Asp Val Leu Val Cys Thr Val Ile Gly Phe Pro
     50                  55                  60

Leu Gly Ala Thr Thr Thr Ala Val Lys Ser Tyr Glu Thr Lys Asp Ala
 65                  70                  75                  80

Ile Asn Asn Gly Ala Gln Glu Ile Asp Met Val Ile Asn Ile Gly Ala
                 85                  90                  95

Leu Lys Asp Gly Arg Phe Asp Glu Val Gln Asn Asp Ile Glu Ala Val
            100                 105                 110

Val Gln Ala Ala Asn Gly Lys Thr Val Lys Val Ile Glu Thr Val
        115                 120                 125

Leu Leu Thr Glu Lys Glu Lys Ile Lys Ala Cys Gln Leu Ser Glu Ala
    130                 135                 140

Ala Gly Ala His Phe Val Lys Thr Ser Thr Gly Phe Ala Gly Gly Gly
145                 150                 155                 160

Ala Thr Val Glu Asp Val Lys Leu Met Lys Asp Thr Val Gly Asp Arg
                165                 170                 175

Leu Glu Val Lys Ala Ser Gly Gly Val Arg Asn Leu Glu Asp Phe Asn
            180                 185                 190

Asn Met Ile Glu Ala Gly Ala Thr Arg Ile Gly Ala Ser Ala Gly Val
        195                 200                 205

Gln Ile Ile Gln Gly Leu Glu Ser Asn Thr Asp Tyr
    210                 215                 220
```

```
<210> SEQ ID NO 40
<211> LENGTH: 648
<212> TYPE: DNA
<213> ORGANISM: Lactobacillus plantarum

<400> SEQUENCE: 40
atgaaattga atcgttattt agatcacacg ttattaaaac cggaagcgac tgagcaacaa     60
attgatcagg tagtacggga ggcactcgaa aatcactttt attcagttat ggtcaatcca    120
tactgggtca agcacgtcca tgcgcaactt gctggttcgg atgttgcgac tgcatgcgtg    180
attggtttcc ctctgggcgc gaatacaacc gccattaaag ttgcggaagc caaacaggca    240
attgctgacg gtgtggatga gctggatatg gtcattaata tcggcgaatt gaaaggcgac    300
cactatgatg cagttcaaca agacattgaa agtgtggtaa cagttggaca tacggctgat    360
```

```
aaggtcgtca aagtgattat tgaaacggcg ctgttgacgg atggggaaat cgttaaggct    420
agtgaaattg ttgccgatgc acacgctgat tttgtgaaga catcgactgg attttcaacc    480
cgtggtgctt cggttcatga tattagtttg atgaaggggtg ccgttcagga tcgaatcggg    540
gtcaaagcat ctgggggaat ccatacacgc gatgaagcat tagcgatgat tgatgctgga    600
gcaacgcgcc tcggtgtatc agcaagtatg gcaattattg gtaagtag                 648
```

<210> SEQ ID NO 41
<211> LENGTH: 215
<212> TYPE: PRT
<213> ORGANISM: Lactobacillus plantarum

<400> SEQUENCE: 41

```
Met Lys Leu Asn Arg Tyr Leu Asp His Thr Leu Leu Lys Pro Glu Ala
1               5                   10                  15

Thr Glu Gln Gln Ile Asp Gln Val Val Arg Glu Ala Leu Glu Asn His
            20                  25                  30

Phe Tyr Ser Val Met Val Asn Pro Tyr Trp Val Lys His Val His Ala
        35                  40                  45

Gln Leu Ala Gly Ser Asp Val Ala Thr Ala Cys Val Ile Gly Phe Pro
    50                  55                  60

Leu Gly Ala Asn Thr Thr Ala Ile Lys Val Ala Glu Ala Lys Gln Ala
65                  70                  75                  80

Ile Ala Asp Gly Val Asp Glu Leu Asp Met Val Ile Asn Ile Gly Glu
                85                  90                  95

Leu Lys Gly Asp His Tyr Asp Ala Val Gln Gln Asp Ile Glu Ser Val
            100                 105                 110

Val Thr Val Gly His Thr Ala Asp Lys Val Val Lys Val Ile Ile Glu
        115                 120                 125

Thr Ala Leu Leu Thr Asp Gly Glu Ile Val Lys Ala Ser Glu Ile Val
    130                 135                 140

Ala Asp Ala His Ala Asp Phe Val Lys Thr Ser Thr Gly Phe Ser Thr
145                 150                 155                 160

Arg Gly Ala Ser Val His Asp Ile Ser Leu Met Lys Gly Ala Val Gln
                165                 170                 175

Asp Arg Ile Gly Val Lys Ala Ser Gly Gly Ile His Thr Arg Asp Glu
            180                 185                 190

Ala Leu Ala Met Ile Asp Ala Gly Ala Thr Arg Leu Gly Val Ser Ala
        195                 200                 205

Ser Met Ala Ile Ile Gly Lys
    210                 215
```

<210> SEQ ID NO 42
<211> LENGTH: 728
<212> TYPE: DNA
<213> ORGANISM: Lactobacillus acidophilus

<400> SEQUENCE: 42

```
cagaggtaaa aattatgaaa tatactttag acgactttgc acgttttaatt gatcacacta    60 acttacacgc tgatgcaact gaagccgata tgaagaagtt atgtgatgaa gcaaagaaat   120
atcattttaa aatggtagct attaatcaag ttcaatccaa gttttgctca gagcaattaa   180
agggaacaga cattgatact ggtgctgcaa ttgcttttcc tttaggacaa caaactattg   240
aatccaaggt atttgatact agggatgcaa ttaagaatgg tgctaatgaa attgattatg   300
tgattaatat tactcaatta aaagctaaag actacgatta tataaagcaa gaaatgcaag   360
```

```
agatggttaa tgcttgtcat gaaaatcatg ttccatgtaa agtgattttt gaaaattgct    420
atttaaccaa agatgaaata aaaaaattag ctgagattgc taagaagta aagcctgact     480 ttattaagac ttctactggc tttggtagtt caggcgctaa ggtagaagac gtaaagctaa    540
tgaaatcaat tgttggcgat gaagtaaaag taaaggctgc cggtggtatt cgtaatagtg    600
atgatttctt agccatggtg cgcgctggtg ctgatagaat tggttgttct gctggagtca    660
aaatttatca gctttaaaag tgtagaatga agacgacca tgtggatagt attgagattg      720
cacgttag                                                              728
```

```
<210> SEQ ID NO 43
<211> LENGTH: 237
<212> TYPE: PRT
<213> ORGANISM: Lactobacillus acidophilus

<400> SEQUENCE: 43

Met Lys Tyr Thr Leu Asp Asp Phe Ala Arg Leu Ile Asp His Thr Asn
1               5                   10                  15

Leu His Ala Asp Ala Thr Glu Ala Asp Met Lys Lys Leu Cys Asp Glu
            20                  25                  30

Ala Lys Lys Tyr His Phe Lys Met Val Ala Ile Asn Gln Val Gln Ser
        35                  40                  45

Lys Phe Cys Ser Glu Gln Leu Lys Gly Thr Asp Ile Asp Thr Gly Ala
    50                  55                  60

Ala Ile Ala Phe Pro Leu Gly Gln Gln Thr Ile Glu Ser Lys Val Phe
65                  70                  75                  80

Asp Thr Arg Asp Ala Ile Lys Asn Gly Ala Asn Glu Ile Asp Tyr Val
                85                  90                  95

Ile Asn Ile Thr Gln Leu Lys Ala Lys Asp Tyr Asp Tyr Ile Lys Gln
            100                 105                 110

Glu Met Gln Glu Met Val Asn Ala Cys His Glu Asn His Val Pro Cys
        115                 120                 125

Lys Val Ile Phe Glu Asn Cys Tyr Leu Thr Lys Asp Glu Ile Lys Lys
    130                 135                 140

Leu Ala Glu Ile Ala Lys Glu Val Lys Pro Asp Phe Ile Lys Thr Ser
145                 150                 155                 160

Thr Gly Phe Gly Ser Ser Gly Ala Lys Val Glu Asp Val Lys Leu Met
                165                 170                 175

Lys Ser Ile Val Gly Asp Glu Val Lys Val Lys Ala Ala Gly Gly Ile
            180                 185                 190

Arg Asn Ser Asp Asp Phe Leu Ala Met Val Arg Ala Gly Ala Asp Arg
        195                 200                 205

Ile Gly Cys Ser Ala Gly Val Lys Ile Tyr Gln Ala Leu Lys Cys Arg
    210                 215                 220

Met Lys Asp Asp His Val Asp Ser Ile Glu Ile Ala Arg
225                 230                 235

<210> SEQ ID NO 44
<211> LENGTH: 672
<212> TYPE: DNA
<213> ORGANISM: Streptococcus pyogenes

<400> SEQUENCE: 44
gtggaagtaa aagatatttt aaaaacggta gaccatactt tgctagcaac aacagcaacg    60
tggccagaaa tccaaacaat tttagatgat gccatggctt atgaaacagc ttcagcatgt   120
attccagctt cttacgtcaa aaaagcagca gaatacgttt caggtaaatt agctatttgt   180
```

```
actgttattg ggttcccaaa tggctatagt acaactgcgg cgaaggtttt tgaatgtcaa    240
gatgctattc aaaatggtgc tgatgaaatt gacatggtca ttaatttgac agacgttaaa    300
aatggggatt ttgatactgt tgaagaagaa attcgtcaaa tcaaagctaa atgtcaagac    360
catatcttaa aagttatcgt tgagacatgt caattaacta aagaagaact tatcgaactt    420
tgtggagttg tcacacgttc aggtgcagac tttattaaaa cctctactgg tttttcgaca    480
gcaggtgcta catttgaaga tgttgaagtg atggcaaaat atgtcggcga aggtgttaaa    540
attaaggcag caggtggaat ctcatcattg gaagatgcta aaacatttat tgctttagga    600
gcttcacgct tgggtactag ccgtatcatc aagattgtta agaacgaagc tacaaaaccc    660
gatagctatt aa                                                         672
```

<210> SEQ ID NO 45
<211> LENGTH: 223
<212> TYPE: PRT
<213> ORGANISM: Streptococcus pyogenes

<400> SEQUENCE: 45

```
Met Glu Val Lys Asp Ile Leu Lys Thr Val Asp His Thr Leu Leu Ala
1               5                   10                  15

Thr Thr Ala Thr Trp Pro Glu Ile Gln Thr Ile Leu Asp Asp Ala Met
            20                  25                  30

Ala Tyr Glu Thr Ala Ser Ala Cys Ile Pro Ala Ser Tyr Val Lys Lys
        35                  40                  45

Ala Ala Glu Tyr Val Ser Gly Lys Leu Ala Ile Cys Thr Val Ile Gly
    50                  55                  60

Phe Pro Asn Gly Tyr Ser Thr Thr Ala Ala Lys Val Phe Glu Cys Gln
65                  70                  75                  80

Asp Ala Ile Gln Asn Gly Ala Asp Glu Ile Asp Met Val Ile Asn Leu
                85                  90                  95

Thr Asp Val Lys Asn Gly Asp Phe Asp Thr Val Glu Glu Glu Ile Arg
            100                 105                 110

Gln Ile Lys Ala Lys Cys Gln Asp His Ile Leu Lys Val Ile Val Glu
        115                 120                 125

Thr Cys Gln Leu Thr Lys Glu Glu Leu Ile Glu Leu Cys Gly Val Val
    130                 135                 140

Thr Arg Ser Gly Ala Asp Phe Ile Lys Thr Ser Thr Gly Phe Ser Thr
145                 150                 155                 160

Ala Gly Ala Thr Phe Glu Asp Val Glu Val Met Ala Lys Tyr Val Gly
                165                 170                 175

Glu Gly Val Lys Ile Lys Ala Ala Gly Gly Ile Ser Ser Leu Glu Asp
            180                 185                 190

Ala Lys Thr Phe Ile Ala Leu Gly Ala Ser Arg Leu Gly Thr Ser Arg
        195                 200                 205

Ile Ile Lys Ile Val Lys Asn Glu Ala Thr Lys Pro Asp Ser Tyr
    210                 215                 220
```

<210> SEQ ID NO 46
<211> LENGTH: 783
<212> TYPE: DNA
<213> ORGANISM: Rhodopirellula baltica

<400> SEQUENCE: 46

```
ttgcgcgaca cccgacctcc tgccgcatcg ctatcgcttc acggaaacct gctcaccatg     60
gctgactatc aatatcacga cgtctccaag atgattgacc actcgctgct tccacccaca    120
```

```
ctgaccgaag cggacttgga ttccggcatc gatttggcaa tcgcttatga agtcgccagc     180
gtttgtatct tgccctacta cttgaaacgt tgtgctgcga agctcgcggg caccggcgtg     240
aaagcgtcaa ccacgatcgg ttttcctcat ggtggtcaca ccaccgcgat caagaaagcc     300
gaagccgaac aagccatcca agatggctgc gaagaactcg acttcgtcgt caacatctcg     360
caagtcctga gcggcggttg ggactacgtc caaaatgaaa ttggcgaggt caccgaactg     420
acccatgcgg ccggacaaaa gatcaaggtg atcttcgaga actgctacct gcaggacgaa     480
cacaagattc gtctgtgcga gatctgcacc gagctcaaag tggactgggt caaaacatcg     540
actggttatg gaactggagg cgcgaccatg gacgacctgc gtctgatgcg acaacactca     600
ggcgaaaacg tccaagtcaa agctgccggt ggcgtccgag atctcgcgac actgctggag     660
gtccgagccc tcggagcatc ccgttgcggt gccagccgaa ccgccgagat gctgggcgaa     720
gcccgaaagc aacttggcat gcccgcgatt gaaatcaccg cgaccggcag ctccggctac     780
tga                                                                   783
```

<210> SEQ ID NO 47
<211> LENGTH: 260
<212> TYPE: PRT
<213> ORGANISM: Rhodopirellula baltica

<400> SEQUENCE: 47

```
Met Arg Asp Thr Arg Pro Pro Ala Ala Ser Leu Ser Leu His Gly Asn
1               5                   10                  15

Leu Leu Thr Met Ala Asp Tyr Gln Tyr His Asp Val Ser Lys Met Ile
            20                  25                  30

Asp His Ser Leu Leu Pro Pro Thr Leu Thr Glu Ala Asp Leu Asp Ser
        35                  40                  45

Gly Ile Asp Leu Ala Ile Ala Tyr Glu Val Ala Ser Val Cys Ile Leu
    50                  55                  60

Pro Tyr Tyr Leu Lys Arg Cys Ala Ala Lys Leu Ala Gly Thr Gly Val
65                  70                  75                  80

Lys Ala Ser Thr Thr Ile Gly Phe Pro His Gly Gly His Thr Thr Ala
                85                  90                  95

Ile Lys Lys Ala Glu Ala Glu Gln Ala Ile Gln Asp Gly Cys Glu Glu
            100                 105                 110

Leu Asp Phe Val Val Asn Ile Ser Gln Val Leu Ser Gly Gly Trp Asp
        115                 120                 125

Tyr Val Gln Asn Glu Ile Gly Glu Val Thr Glu Leu Thr His Ala Ala
    130                 135                 140

Gly Gln Lys Ile Lys Val Ile Phe Glu Asn Cys Tyr Leu Gln Asp Glu
145                 150                 155                 160

His Lys Ile Arg Leu Cys Glu Ile Cys Thr Glu Leu Lys Val Asp Trp
                165                 170                 175

Val Lys Thr Ser Thr Gly Tyr Gly Thr Gly Gly Ala Thr Met Asp Asp
            180                 185                 190

Leu Arg Leu Met Arg Gln His Ser Gly Glu Asn Val Gln Val Lys Ala
        195                 200                 205

Ala Gly Gly Val Arg Asp Leu Ala Thr Leu Leu Glu Val Arg Ala Leu
    210                 215                 220

Gly Ala Ser Arg Cys Gly Ala Ser Arg Thr Ala Glu Met Leu Gly Glu
225                 230                 235                 240

Ala Arg Lys Gln Leu Gly Met Pro Ala Ile Glu Ile Thr Ala Thr Gly
                245                 250                 255
```

```
Ser Ser Gly Tyr
            260

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgggatccac tgatctgaaa gcaagcagcc                                    30

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcaagcttgc tgctggcgct cttacc                                        26
```

((2S,4R)-4,6-DIHYDROXYTETRAHYDRO-2H-PYRAN-2-YL)METHYL CARBOXYLATE AND PROCESS FOR THE PRODUCTION THEREOF

CROSS-REFERENCE TO RELATED APPLICATIONS

This application is a 371 U.S. National Phase of International Patent Application No. PCT/EP2009/050583 filed Jan. 20, 2009, which claims priority to European Patent Application No. 08100845.0 filed Jan. 23, 2008, the entire contents of which are herewith incorporated by reference.

SEQUENCE LISTING

The instant application contains a Sequence Listing which has been submitted in ASCII format via EFS-Web and is hereby incorporated by reference in its entirety. Said ASCII copy, created on Oct. 25, 2010, is named 30308016.txt and is 72,028 bytes in size.

FIELD OF THE INVENTION

The present invention relates to ((2S,4R)-4,6-dihydroxytetrahydro-2H-pyran-2-yl)methyl carboxylates and a process for the production thereof. Furthermore, the present invention relates to a process for the production of statins and in particular of Rosuvastatin and derivates thereof, wherein the above mentioned compounds are used as intermediates.

BACKGROUND OF THE INVENTION ((2S,4R)-4,6-dihydroxytetrahydro-2H-pyran-2-yl)methyl carboxylate is a possible intermediate in the synthesis of statins. Statins, the representative examples of which may be selected from rosuvastatin, cerivastatin, atorvastatin, fluvastatin, pitavastatin, bervastatin, dalvastatin or their analogs or pravastatin, simvastatin, lovastatin or their analogs share a characteristic structure defined by respectively a heptenoic or heptanoic acid moiety (free acid, salt or lactone) connected to the aromatic or alicyclic core. Biological activity of statins is closely related to their stereochemistry, especially configuration at the chiral atoms of said heptenoic or heptanoic acid moiety.

In WO 2006/134482, a 2-deoxyribose-5-phophate aldolase (DERA) catalyzed aldol addition step is included in a process for forming atorvastatin.

JP 2005229858 discloses a method for producing ((4R, 6S)-4,6 dihydroxytetrahydro-2-pyrone, wherein benzyloxyacetaldehyde is reacted with acetaldehyde in the presence of DERA. The reaction time of the enzymatic catalysis was 12 h.

WO 05/118794 deals with an improvement of the DERA enzyme. The isolated mutant enzymes may be used for the preparation of a 2,4-dideoxyhexose or a 2,4,6 trideoxyhexose having a high variety of substituents.

A DERA mutant was described catalyzing stereospecific aldol reaction (Tetrahedron Letters 2004, 45, 2439-2441). The DERA mutant showed a relative improvement in catalytic activity, and thus improved yields compared with the wild type DERA. The reaction time of the enzymatic catalysis was 6 days. One product obtained from this enzymatic catalysis was proposed for the synthesis of atorvastatin.

A DERA for catalyzing stereospecific aldol reaction was further described in Proc. Nat. Acad. Sci. USA 2004, 101 (16) 5788-5793, showing improved volumetric productivity of the enzymatic process. The inhibitory effects of the substrates used towards enzyme activity are also described. The reaction time of the enzymatic catalysis was 3 h. The products obtained from this enzymatic catalysis were proposed for the synthesis of atorvastatin or rosuvastatin A stereospecific aldol reaction with three aldehyde substrates catalyzed by 2-deoxyribose-5-phophate aldolase (DERA) does not equally accept all substituted acetaldehydes as substrates for DERA (Am. Chem. Soc.; 117, 29, (1995) pp 7585) and certain substrates show inhibitory effects on DERA activity. The reaction time of the enzymatic catalysis was 6 days.

In WO 2007/039287 A1, a synthesis of lactonized statin side chains intermediate VI via iodolactone synthesis is described, which requires 6 organic synthetic steps. In this multiple step synthesis, the 4$^{th}$ step is a lactone forming step defining the stereochemistry of the iodolactone intermediate product. This lactone forming step provides relatively low stereoselectivity only. Some reagents used in stoichiometric amount like the I-compounds, the Ag-compound, the Grignard reagent and the enantiopure starting compound are quite expensive. The 6 steps of organic synthesis (shown in the following) gave a total yield of 19%:

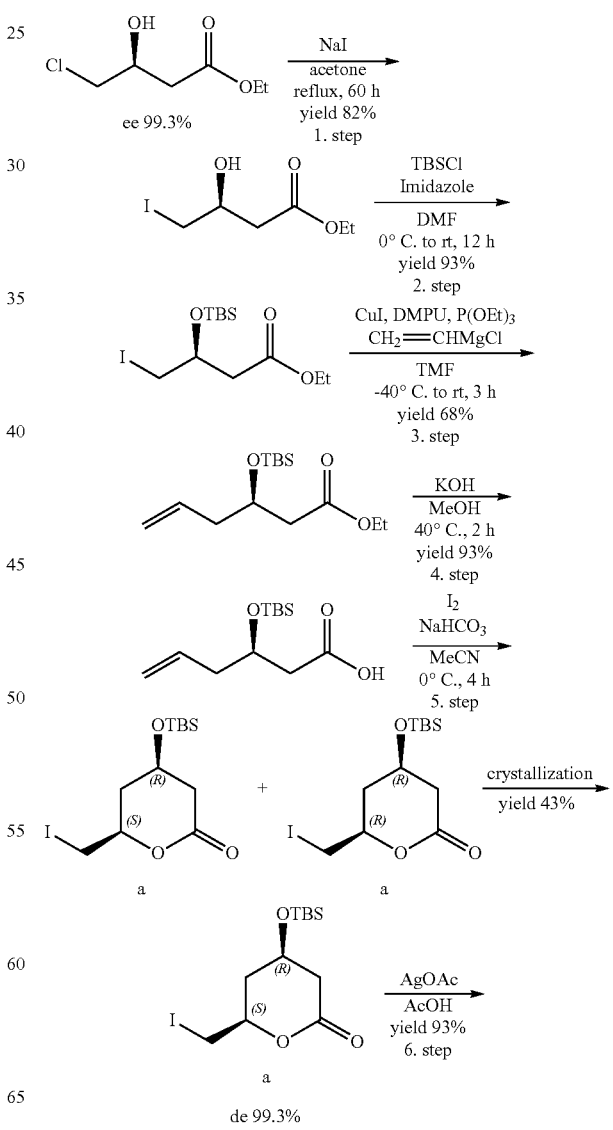

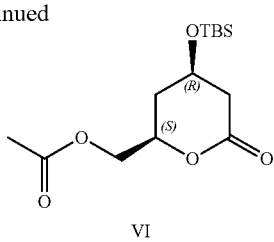

The object of the present invention is to provide intermediate compounds and processes as building blocks for effectively producing statins.

DISCLOSURE OF THE INVENTION

The object is solved by providing ((2S,4R)-4,6-dihydroxytetrahydro-2H-pyran-2-yl)methyl carboxylates by a process requiring few synthetic steps, showing relatively short reaction times and resulting in a high overall yield of a product having high stereochemical purity concerning enantiomeric and diastereomeric excess. A further object of the invention is to produce the above mentioned carboxylate with inexpensive starting materials and simple equipment.

An aspect of the invention is a process for preparing a compound of formula IV

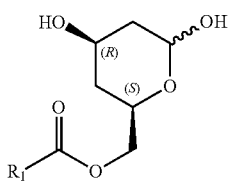

wherein $R_1$=alkyl, alkoxy, aryl, heteroaryl, arylalkyl or heteroarylalkyl, respectively and independently substituted or not substituted, which comprises the step of bringing in contact acetaldehyde and an aldehyde of the formula III $R_1CO_2CH_2CHO$, wherein $R_1$ is defined as above, with an enzyme catalyzing aldol condensation. By preferably using an enzyme catalyzing sequential aldol reactions, the number of reaction steps to arrive at IV can be reduced.

Preferably, the substrate is selected among a compound of formula III, wherein $R_1$=$C_1$-$C_6$ alkyl or alkoxy, respectively and independently substituted or not substituted. Selection of such appropriate enzyme substrate enables substantially shortened reaction times and provide remarkably improved stereoselectivity of the reaction. Appropriate selection of the substrate further allows the substrate to be controlled, as the enzymatic reaction is carried out in an aqueous medium. Furthermore, the ester moiety of IV is selected to be preferably not cleavable by water. Thus, more preferably $R_1$=$CH_3$. In particular, appropriate enzyme substrates are preferably selected to provide the compound of formula IV having enantiomeric excess of 99.8% or more and/or diastereomeric excess of 98% or more. A high enantiomeric and diastereomeric excess is a significant advancement, because purification and isolation of the product is easier then and the yield is accordingly higher. It is preferred that the enzyme is 2-Deoxyribose-5-phosphate aldolase (DERA, EC 4.1.2.4). It may be useful to screen different types of DERA enzymes in order to find an enzyme having broader substrate specificity. Furthermore, a DERA enzyme may be tailored for a specific substrate. For these reasons, different mutant DERA enzymes may be tested. More particular, said aldolase is selected from the group consisting of DERA 01, DERA 02, DERA 03, DERA 04, DERA 05, DERA 06, DERA 07, DERA 08, DERA 09, DERA 10, DERA 11, DERA 12 DERA 13, DERA 14, DERA 15, DERA 16, DERA 17, DERA 18, DERA 19, DERA 20, DERA 21 DERA 22 and DERA 23 or an aldolase having an amino acid sequence identity of at least about 70% to amino acid sequence of any of said aldolases. More particular said aldolase is selected from the group consisting of DERA 01, DERA 02, DERA 05, DERA 12 and DERA 13 and in particular wherein said aldolase has an amino acid sequence identity of at least about 70% to amino acid sequence of SEQ ID NO: 2 or wherein said aldolase has an amino acid sequence identity of at least about 80% to amino acid sequence of SEQ ID NO: 5 or wherein said aldolase has an amino acid sequence identity of at least about 80% to amino acid sequence of SEQ ID NO: 11 or wherein said aldolase has an amino acid sequence identity of at least about 80% to amino acid sequence of SEQ ID NO: 25. or wherein said aldolase has an amino acid sequence identity of at least about 80% to amino acid sequence of SEQ ID NO: 27.

In one preferred embodiment the step of bringing in contact acetaldehyde and an aldehyde of the formula III $R_1CO_2CH_2CHO$ is accomplished by contacting acetaldehyde and said aldehyde of the formula III with a microorganism or a part of microorganism, respectively, over expressing biologically active form of aldolase. Said contacting step is performed such that aldol condensation is catalysed. According to this embodiment aldolase over expressing organism as whole cell catalysts is used. The possibility to use aldolase over expressing organisms as whole cell catalysts additionally allows lower production costs compared to process described in Proc. Nat. Acad. Sci. USA 2004, 101 (16) 5788-5793 as several steps in enzyme preparation and purification of product are omitted. Also, stabilizing effect of cell environment allows use of higher substrate concentrations with lower impact to enzyme activity compared to other enzyme preparations. This allows higher volumetric productivity with lower enzyme loads, which significantly reduces production costs. Surprisingly using aldolase over expressing organisms as whole cell catalysts high enantiomeric and diastereomeric excess of the compound of formula IV is retained.

Another aspect of the invention is a process for preparing a compound of formula IV

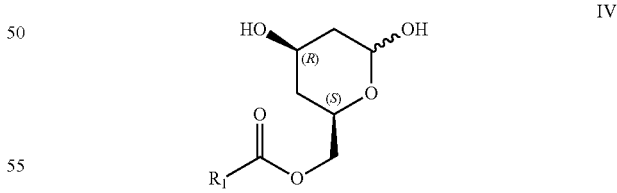

wherein $R_1$=alkyl, alkoxy, aryl, heteroaryl, arylalkyl or heteroarylalkyl, respectively and independently substituted or not substituted, which comprises the step of bringing in contact acetaldehyde and an aldehyde of the formula III, $R_1CO_2CH_2CHO$, wherein $R_1$ is defined as above, with microorganism or a part of microorganism, respectively, over expressing biologically active form of aldolase. Said contacting step is performed such that aldol condensation is catalysed. According to this aspect of the invention aldolase over expressing organism as whole cell catalysts is used.

Preferably enzyme in the form of whole cell catalyst is 2-Deoxyribose-5-phosphate aldolase (DERA, EC 4.1.2.4).

Another aspect of the invention is a process for preparing a compound of formula IV

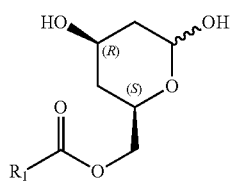

wherein $R_1$=alkyl, alkoxy, aryl, heteroaryl, arylalkyl or heteroarylalkyl, respectively and independently substituted or not substituted, which comprises the step of bringing in contact acetaldehyde and an aldehyde of the formula III, $R_1CO_2CH_2CHO$, wherein $R_1$ is defined as above, with an enzyme catalyzing aldol condensation, wherein said enzyme is in the form of whole cell catalyst, wherein said whole cell catalyst is an microorganism over expressing biologically active form of aldolase.

Another aspect of the invention is a process for preparing a compound of formula XV

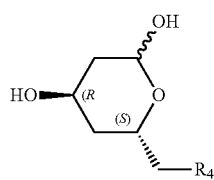

wherein $R_4$=OCOR$_1$ (wherein $R_1$ is as defined above), chloride, hydrogen, allyloxy and benzyloxy respectively and independently substituted or not substituted, which comprises the step of bringing in contact acetaldehyde and an aldehyde of the formula XIV, $R_4CH_2CHO$ wherein $R_4$ is defined as above, with microorganism or a part of microorganism, respectively, over expressing biologically active form of aldolase. Said contacting step is performed such that aldol condensation is catalysed. According to this aspect of the invention aldolase over expressing organism as whole cell catalysts is used.

Preferably enzyme in the form of whole cell catalyst is 2-Deoxyribose-5-phosphate aldolase (DERA, EC 4.1.2.4).

Another aspect of the invention is a process for preparing a compound of formula XV

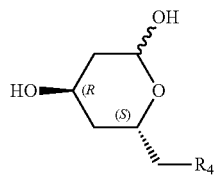

wherein $R_4$=OCOR$_1$, (wherein $R_1$ is as defined above), chloride, hydrogen, allyloxy and benzyloxy respectively and independently substituted or not substituted, which comprises the step of bringing in contact acetaldehyde and an aldehyde of the formula XIV, $R_4CH_2CHO$ wherein $R_4$ is defined as above, with an enzyme catalyzing aldol condensation, wherein said enzyme is in the form of whole cell catalyst, wherein said whole cell catalyst is an microorganism over expressing biologically active form of aldolase.

Significantly lower process costs are achieved when an enzyme in the form of whole cell catalyst is used, as several steps in enzyme preparation and purification of product are omitted. Also, stabilizing effect of cell environment allows use of higher substrate concentrations with lower impact to enzyme activity compared to other enzyme preparations. Furthermore high enantiomeric and diastereomeric excess is obtained when using an enzyme in the form of whole cell catalyst The process aspect of invention can be effectively accomplished in reaction conditions wherein pH for aldolase-catalysed aldol condensation is maintained in the range of 4.5 to 10, preferably 5 to 10, in particular wherein pH is maintained with a buffer in the pH range of 5 to 8, preferably 5 to 7 An appropriate pH value results in shorter reaction times. In another aspect appropriate pH reduces substrate and/or product degradation. A buffer allows to adjust the pH-value to a constant level, which contributes to constant reaction conditions concerning the pH-value. To this end, the buffer is preferably a phosphate buffer. Alternatively, a precise pH control can be achieved by an automated addition of an acid or an alkali with the assistance of a pH regulated pump.

Another aspect of the invention is a use of aldolase for the reaction of a substrate of the formula III, $R_1CO_2CH_2CHO$, wherein $R_1$ is as defined above, with acetaldehyde under aldolase-catalysed aldol condensation conditions to form a compound of formula IV, wherein $R_1$ is defined as above, which comprises the step of bringing in contact acetaldehyde and an aldehyde of the formula III, $R_1CO_2CH_2CHO$. In particular, said aldolase is 2-deoxyribose-5-phosphate aldolase. More particular, aldolase is selected from the group consisting of DERA 01 to DERA 23 as described above. In particular said aldolase is comprised within living whole cell, or is comprised within inactivated whole cell, or is comprised within homogenized whole cell, or is comprised within cell free extract, or is purified enzyme, or is immobilized, or is in form of extracellularly expressed protein.

Another aspect of the invention is a process for preparing a compound of formula V

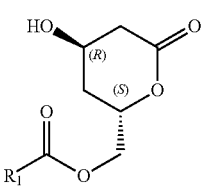

wherein $R_1$=alkyl, alkoxy, aryl, heteroaryl, arylalkyl or heteroarylalkyl, respectively and independently substituted or not substituted, which comprises the step of converting the compound of formula IV, by oxidation into the compound of formula V. The reactants for the oxidation should be inexpensive and afford a high yield. Thus, the oxidation is preferably performed with $Br_2$ and $BaCO_3$.

In particular compound of formula V having enantiomeric excess of 99.8% or more and/or diastereomeric excess of 98% or more is provided.

Another aspect of the present invention is a process for the production of an aldehyde of the formula III', $R_2CO_2CH_2CHO$, wherein $R_2$ is alkyl, alkoxy, aryl, heteroaryl, arylalkyl or heteroarylalkyl, respectively and independently substituted or not substituted, excluding n-propyl, cyclohexyl, phenyl, morpholine, pyrrolidine and imidazole, which process comprises the steps of
a.) bringing a compound of the formula II, $R_2CO_2CH_2CH=CHCH_2O_2CR_2$,

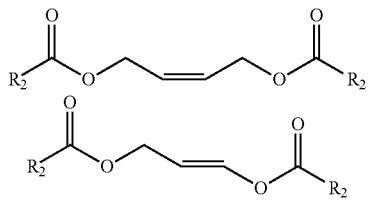

wherein $R_2$ is defined as above, in contact with a solvent and with ozone, and
b.) hydrolyzing the ozonide resulting from the step a).

Ozonolysis provides inexpensive production of said aldehyde with a high yield. Especially a (Z)- and/or (E)-alkene having two identical substituents besides H in (Z)- and/or (E)-position provides high molecular economics, as 2 desired products are obtained after hydrolysis, while conversion of a (Z)- and/or (E)-alkene having two different substituents besides H in (Z)- and/or (E)-position provides one desired product and one waste product. In particular, the solvent of step a) is dichloromethane. Preferably, $R_2$ is $C_1$-$C_6$ alkyl or alkoxy, excluding n-propyl, cyclohexyl. More preferably, $R_2$ is $CH_3$. It is preferred to carry out step a) at a temperature in the range of −50 to −90° C., more preferably at about −80° C. Furthermore, it is preferred to carry out step b) by bringing the resulting ozonide of step a) in contact with methylsulfide. In particular, step b) is carried out at a temperature comprised between −80° C. and room temperature.

Compounds of formula II are obtained by reacting (Z)- and/or (E)-but-2-ene-1,4-diol with an anhydride of the formula I $R_2CO_2COR_2$ wherein $R_2$ is defined as above and as described in example 1 step 1 or as in prior art synthesis (*J. Org. Chem.* 1956, 21, 328-331). Another aspect of the present invention is a compound of formula IV or V

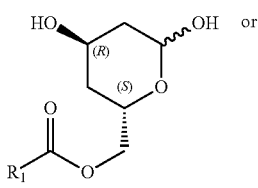

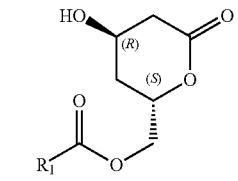

wherein $R_1$=alkyl, alkoxy, aryl, heteroaryl, arylalkyl or heteroarylalkyl, respectively and independently substituted or not substituted. The compounds of formula IV or V wherein $R_1$=$C_1$-$C_6$ alkyl or alkoxy, respectively and independently substituted or not substituted, and in particularly wherein $R_1$=$CH_3$ are preferred.

Still another aspect of the present invention is a process for the production of a statin or a derivative thereof, comprising the steps of:
a) protecting a compound of formula V

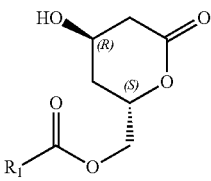

TECH/881253.1 wherein $R_1$=alkyl, alkoxy, aryl, heteroaryl, arylalkyl or heteroarylalkyl, respectively and independently substituted or not substituted; at the hydroxy group at the 4-position by a protective group $R_3$ (wherein $R_3$ is a protecting group, preferably selected from independently substituted or not substituted silyl, benzyl, alkyl and acetyl, more preferably $R_3$ is selected from optionally substituted $C_1$-$C_8$ trialkylsilyl, $C_1$-$C_8$ dialkylarylsilyl, $C_1$-$C_8$ alkyldiarylsilyl, wherein alkyls may be same or different, more preferably protecting group is tert-butyldimethylsilyl) to give a compound of formula VI

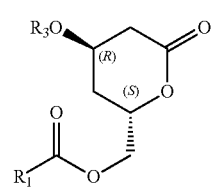

b) reacting said compound of formula VI under conditions sufficient to produce statin
or a pharmaceutically acceptable derivative thereof.

In particular compound of formula VI having enantiomeric excess of 99.8% or more and/or diastereomeric excess of 98% or more is provided.

In the process for the production of a statin or a derivative thereof, it is preferred that the conditions of step b) are set by conversion of VI to an aldehyde and by a Wittig coupling with an appropriate phosphonium salt or other phosphorus derivative to give a statin or a derivative thereof. Still more preferably, the Wittig coupling step comprises the steps of:
b1) Providing aldehyde having the formula VIII from compound of formula VI
b2) Providing a phosphonium salt having the formula IX

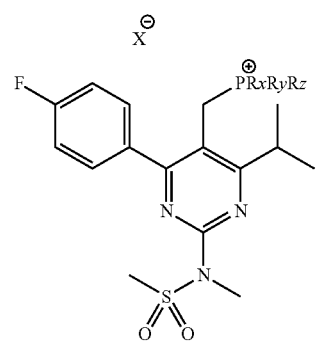

wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_6$-$C_6$ cycloalkenyl or aryl, and X is an anion, preferably a halogen or carboxylate anion, more preferably chloride, bromide or trifluoroacetate;

to give a compound of formula X

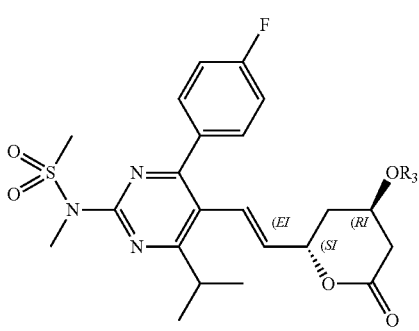

X b3) subsequently converting compound X to Rosuvastatin or its salt.

Said step b1) of providing aldehyde having the formula VIII from compound of formula VI is performed through compound of formula VII,

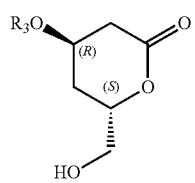

VII wherein $R_3$ is defined as above.

In particular compound of formula VII having enantiomeric excess of 99.8% or more and/or diastereomeric excess of 98% or more is provided.

Still another aspect of the present invention is a process for the production of a statin or a derivative thereof, comprising the steps of:

a) preparing a compound of formula IV

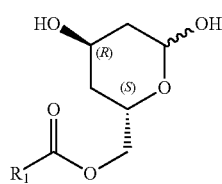

IV wherein $R_1$=alkyl, alkoxy, aryl, heteroaryl, arylalkyl or heteroarylalkyl, respectively and independently substituted or not substituted, which comprises the step of bringing in contact acetaldehyde and an aldehyde of the formula III, $R_1CO_2CH_2CHO$, wherein $R_1$ is defined as above, with an enzyme catalyzing aldol condensation.

b) converting said compound of formula IV by oxidation into the compound of formula V

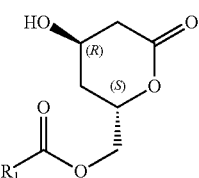

V wherein $R_1$ is as defined above c) protecting said compound of formula V
at the hydroxy group at the 4-position by a protective group $R_3$ (wherein $R_3$ is a protecting group, preferably selected from independently substituted or not substituted silyl, benzyl, alkyl and acetyl, more preferably $R_3$ is selected from optionally substituted $C_1$-$C_8$ trialkylsilyl, $C_1$-$C_8$ dialkylarylsilyl, $C_1$-$C_8$ alkyldiarylsilyl, wherein alkyls may be same or different, more preferably protecting group is tert-butyldimethylsilyl) to give a compound of formula VI

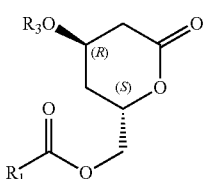

VI d) reacting said compound of formula VI under conditions sufficient to produce statin or a pharmaceutically acceptable derivative thereof, wherein the conditions of step d) are set by conversion of VI to an aldehyde and by a Wittig coupling with an appropriate phosphonium salt or other phosphorus derivative to give a statin or a derivative thereof, preferably the Wittig coupling step comprises the steps of:

b1) Providing aldehyde having the formula VIII from compound of formula VI b2) Providing a phosphonium salt having the formula IX

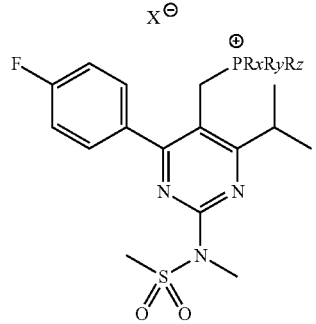

IX wherein Rx, Ry, and Rz, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, and X is an anion, preferably a halogen or carboxylate anion, more preferably chloride, bromide or trifluoroacetate;

to give a compound of formula X

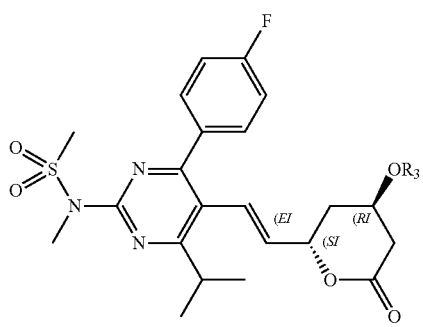

b3) subsequently converting compound X to Rosuvastatin or its salt.

DETAILED DESCRIPTION OF THE INVENTION

In the following, the present invention will be described in more detail by preferred embodiments and examples while referring to the attached drawing, noting, however, that these embodiments, examples and drawing are presented for illustrative purposes only and shall not limit the invention in any way.

FIG. 1 shows the reaction profile of enzymatic reaction according to Example 6.

The present invention provides compounds of the formula IV, which is chemically ((2S,4R)-4,6-dihydroxytetrahydro-2H-pyran-2-yl)methyl carboxylate of general formula:

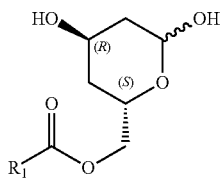

wherein $R_1$=alkyl, alkoxy, aryl, heteroaryl, arylalkyl or heteroarylalkyl, respectively and independently substituted or not substituted.

The feature of the compound of formula IV, in particular when $R_1$ is $C_1$-$C_6$ alkyl or alkoxy, respectively and independently substituted or not substituted, and especially when $R_1$ is $CH_3$ resides in that it possesses the desired stereochemistry, avoiding subsequent separations of later intermediates. Therefore, the provision of intermediate compound IV allows for possible sequential selective oxidation steps or appropriate functional modifications, e.g. involving a first oxidation step of the hydroxy group at the 6-position, optionally a second oxidation step of the hydroxy group at the 4-position, and in addition or alternatively, a third oxidation step at the methoxy group after cleavage of the $R_1$ acyl residue.

The invention provides enzymatic process using compound of the substituted acetaldehyde $R_1CO_2CH_2CHO$ (formula III) and acetaldehyde to form corresponding lactole IV in an aldolase catalysed aldol condensation reaction as presented on following scheme:

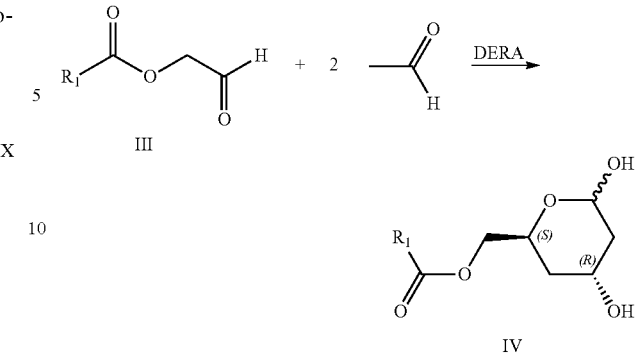

wherein $R_1$ is selected from alkyl, alkoxy, aryl, heteroaryl, arylalkyl or heteroarylalkyl, respectively and independently substituted or not substituted. Structure IV according to the invention has a strictly defined stereoisomery at position 2 and 4, while other chiral centers may be present in both possibilities forming mixtures of epimers.

The term "aldolase-catalyzed aldol condensation conditions" as used herein refers to any aldol condensation conditions known in the art that can be catalyzed by an aldolase, as described herein. In particular the aldolase-catalysed aldol condensation conditions are such that allow forming and accumulation of desired product. These conditions include in one aspect that the aldolase is an active enzyme provided at sufficient load to be able to perform the sequential condensation, in another aspect that the substrate and acetaldehyde are present in the reaction in an amount that displays minimal inhibition of the activity of the aldolase, in another aspect that the temperature, pH, solvent composition, agitation and length of reaction allow accumulation of desired product, in another aspect that said conditions do not have detrimental effect on product stability. Specifically those conditions are defined by values disclosed in examples.

Aldolase activity towards the above compound of formula III means that specified enzyme is either isolated and or purified, or immobilized or within living cell, or comprised within inactivated whole cell, or comprised in homogenized cell material, or in cell free extract which will catalyze the above reaction of compound of formula III and acetaldehyde arriving at IV.

The term "conditions sufficient to produce statin (in particular rosuvastatin) or a pharmaceutically acceptable salt thereof" as used herein refers to those means described in the art to obtain a desired statin compound, including those means described herein.

The term an "organism over expressing biologically active form of an aldolase" as used herein refers to any organism having the aldolase expression under control of a strong promoter, and where the aldolase is expressed at high levels (compared to w.t. expression control) and is accumulated intracellularly or extracellularly. The process of making such organism is well known to a person skilled in the art.

An aldolase for use in the present invention may be any compound that has aldolase activity towards above compound of formula III. In one embodiment of the invention, the aldolase is a 2-deoxyribose-5-phosphate aldolase (DERA). Examples of a suitable DERA—aldolase include, but are not limited to: DERA 01, DERA 02, DERA 03, DERA 04, DERA 05, DERA 06, DERA 07, DERA 08, DERA 09, DERA 10, DERA 11, DERA 12, DERA 13, DERA 14, DERA 15, DERA 16, DERA 17, DERA 18, DERA 19, DERA 20, DERA 21, DERA 22 and DERA 23 which are identified by their nucleotide sequences or respective codon optimized nucleotide sequences or amino acid sequences set forth in sequence listings.

In general, any of the DERA aldolases known in art may be used for the reaction regardless of their sequence identity to the above listed DERA aldolases. The invention provides examples of performing said reactions successfully with two different aldolases having only 30.1% identity. The yields of the reaction however may depend on each aldolases substrate specificity and inhibitory effects of the substrates on each aldolase.

DERA 01 is an aldolase having a nucleotide sequence of SEQ ID NO: 1 or an amino acid sequence of SEQ ID NO: 2; DERA 01 (*E. Coli*) is commercially available from Sigma Aldrich, St. Louis, Mo., USA, under catalog number 91252.

DERA 02 is an aldolase having a nucleotide sequence of SEQ ID NO: 3 or SEQ ID NO: 4 or an amino acid sequence of SEQ ID NO: 5; DERA 02 is described in William A. Greenberg, et al., PNAS, (2004), Vol. 101, No. 16, pp. 5788

DERA 03 is an aldolase having a nucleotide sequence of SEQ ID NO: 6 or an amino acid sequence of SEQ ID NO: 7

DERA 04 is an aldolase having a nucleotide sequence of SEQ ID NO: 8 or an amino acid sequence of SEQ ID NO: 9

DERA 05 is an aldolase having a nucleotide sequence of SEQ ID NO: 10 or an amino acid sequence of SEQ ID NO: 11

DERA 06 is an aldolase having a nucleotide sequence of SEQ ID NO: 12 or an amino acid sequence of SEQ ID NO: 13

DERA 07 is an aldolase having a nucleotide sequence of SEQ ID NO: 14 or an amino acid sequence of SEQ ID NO: 15

DERA 08 is an aldolase having a nucleotide sequence of SEQ ID NO: 16 or an amino acid sequence of SEQ ID NO: 17

DERA 09 is an aldolase having a nucleotide sequence of SEQ ID NO: 18 or an amino acid sequence of SEQ ID NO: 19

DERA 10 is an aldolase having a nucleotide sequence of SEQ ID NO: 20 or an amino acid sequence of SEQ ID NO: 21

DERA 11 is an aldolase having a nucleotide sequence of SEQ ID NO: 22 or an amino acid sequence of SEQ ID NO: 23

DERA 12 is an aldolase having a nucleotide sequence of SEQ ID NO: 24 or an amino acid sequence of SEQ ID NO: 25

DERA 13 is an aldolase having a nucleotide sequence of SEQ ID NO: 26 or an amino acid sequence of SEQ ID NO: 27

DERA 14 is an aldolase having a nucleotide sequence of SEQ ID NO: 28 or an amino acid sequence of SEQ ID NO: 29

DERA 15 is an aldolase having a nucleotide sequence of SEQ ID NO: 30 or an amino acid sequence of SEQ ID NO: 31

DERA 16 is an aldolase having a nucleotide sequence of SEQ ID NO: 32 or an amino acid sequence of SEQ ID NO: 33

DERA 17 is an aldolase having a nucleotide sequence of SEQ ID NO: 34 or an amino acid sequence of SEQ ID NO: 35

DERA 18 is an aldolase having a nucleotide sequence of SEQ ID NO: 36 or an amino acid sequence of SEQ ID NO: 37

DERA 19 is an aldolase having a nucleotide sequence of SEQ ID NO: 38 or an amino acid sequence of SEQ ID NO: 39

DERA 20 is an aldolase having a nucleotide sequence of SEQ ID NO: 40 or an amino acid sequence of SEQ ID NO: 41

DERA 21 is an aldolase having a nucleotide sequence of SEQ ID NO: 42 or an amino acid sequence of SEQ ID NO: 43

DERA 22 is an aldolase having a nucleotide sequence of SEQ ID NO: 44 or an amino acid sequence of SEQ ID NO: 45

DERA 23 is an aldolase having a nucleotide sequence of SEQ ID NO: 46 or an amino acid sequence of SEQ ID NO: 47

The aldolase comprises aldolase having an amino acid sequence identity of at least about 50% thereof; preferably, at least 70% thereof, to a aldolases described herein. The amino acid sequence identities are determined by analysis with sequence comparison algorithm or by visual inspection. In one aspect, the sequence comparison algorithm is made with AlignX algorithm of Vector NTI 9.0 (InforMax) with settings set to default.

In particular the invention provides for a process for preparing a compound of formula IV

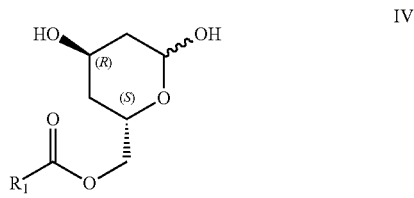

wherein $R_1$=alkyl, alkoxy, aryl, heteroaryl, arylalkyl or heteroarylalkyl, respectively and independently substituted or not substituted, which comprises the step of bringing in contact acetaldehyde and an aldehyde of the formula III, $R_1CO_2CH_2CHO$, wherein $R_1$ is defined as above, with an enzyme catalyzing aldol condensation condition.

In a preferred embodiment, the aldolase is selected from DERA 01 or DERA 02 or DERA 05, or DERA 12, or DERA 13, or any aldolase having an amino acid sequence identity of at least about 90% to those or in another embodiment wherein the aldolase is selected in a preferred embodiment from DERA 06 or DERA 17, or any aldolase having an amino acid sequence identity of at least about 80% to those.

Compound IV is particularly valuable in subsequent use in the synthesis of statins (in particular rosuvastatin).

The DERA aldolases described herein can be prepared by any means known in the art, including but not limited to standard protocols for protein expression in recombinant *E. coli* such as described in Sambrook and Russell, Molecular Cloning: A Laboratory Manual, 3$^{rd}$ Ed., Cold Spring Harbor, N.Y. 2001. Modified versions of known DERA aldolases may be necessary or may result depending on cloning conditions and are encompassed by the present invention.

The DERA aldolases described herein can be used in any biologically active form.

In one embodiment the aldolase is active and can be used in the form of living whole cell catalyst. In one embodiment the aldolase is active and can be used in the form of inactivated whole cell catalyst.

The whole cell catalyst in one embodiment is any microorganism or part of the microorganism over expressing biologically active form of an aldolase. Said microorganism may be in the form of living or resting or inactivated whole cells. These forms may include cell suspensions, cell mycelia, cell pastes and any other forms of microorganism cultures where cells are not intentionally physically, chemically or biologically disrupted, these forms may further include carrier supported, immobilized or adhered forms of such microorganisms or parts thereof.

Said microorganism is preferably selected from Bacteria and Yeast. Bacteria is preferably selected from the group of genera consisting of *Escherichia, Corynebacterium, Pseudomonas, Streptomyces, Rhodococcus, Bacillus*, and *Lactobacillus*, more preferably *Escherichia coli* is used. Yeast is preferably selected from the group of genera consisting of *Saccharomyces, Pichia, Shizosaccharomyces* and *Candida*.

In one embodiment the aldolase is active and can be used in the form of homogenized whole cell catalyst. In one embodiment the aldolase is active and can be used in the form of cell free extract. In one embodiment the aldolase is active and can be used in form purified enzyme by means of any methods known in the art. In another aspect the aldolase is active and can be used in form of extracellularly expressed protein.

Substrates and reaction conditions were chosen to give optimum activity of an aldolase used to make the intermediates useful for statin production.

The compounds of formula III are selected according to the corresponding compound of formula IV product stability at optimal reaction conditions. In particular the acceptor substrates yielding a product with the best stability are preferred for the reaction.

The compounds of formula III are also selected according to the corresponding compound of formula VI, these products having a masked aldehyde group are key intermediates in WO 2007/039287 A1 allowing further steps in preparation of statins, in particular, substrates yielding a product with aldehyde group are preferred.

The compound of formula III may be in particular acetyloxyacetaldehyde ($CH_3CO_2CH_2CHO$).

Generally aldolase will be provided in a suitable vessel or reactor, and the compound of formula III and acetaldehyde will be added batch-wise or continuously.

Specifically aldolase is prepared in an aqueous solution (particularly in a concentration range from 0.1 g/L to 30 g/L) optionally in presence of salt (in particular NaCl in concentration range from 50 to 500 mM) The aqueous solution may contain organic solvents miscible with water (in particular dimethyl sulfoxide in concentration from 2 to 15% V/V), and may be buffered to pH 4.5 to 9, preferably to pH 5 to 9, more preferably to pH 6 to 9.

Suitable buffers can be prepared from: acids, bases, salts or mixtures thereof, and any other buffer system known in the art except those possessing primary, secondary or tertiary amino group. In particular, phosphate buffer, in concentration 10 to 500 mM can be used. The aqueous solution can also be prepared by adding the said aldolase to water and maintaining pH during the reaction by means of automated addition of inorganic acids, bases, salts or mixtures thereof.

Alternatively aldolase is prepared in an aqueous suspension of DERA over expressing cells, particularly DERA over expressing E. coli cells (particularly in a concentration range from 20 g/L to 300 g/L wet cell weight, more particularly in a concentration range from 20 g/L to 200 g/L wet cell weight) optionally in the presence of a salt (in particular NaCl in a concentration from 50 to 500 mM). The aqueous suspension may contain organic solvents miscible with water (in particular dimethyl sulfoxide in a concentration range from 2 to 15% V/V), and may be buffered to pH 4.5 to 9, preferably to pH 5 to 9, more preferably to pH 6 to 9. Suitable buffers can be prepared from: acids, bases, salts or mixtures thereof and any other buffer system known in the art except those possessing primary, secondary or tertiary amino group. In particular, phosphate buffer, in a concentration of 10 to 500 mM can be used. The aqueous suspension can also be prepared by adding said DERA over expressing cells to water and maintaining pH during the reaction by means of an automated addition of inorganic acids, bases, salts or mixtures thereof.

In the process aspect, the compound of formula III may be added to the reaction mixture continuously or alternatively the compound of formula III is added to the reaction mixture in one batch or more batches. In one aspect, the total amount of substrates added to the mixture is such that the total amount of compound of formula III added would be from about 20 mmol per liter of reaction mixture to about 2 mol per liter of reaction mixture, in particular from about 100 mmol per liter of reaction mixture to about 1.5 mol per liter of reaction mixture, more particular from about 200 mmol per liter of reaction mixture to about 700 mmol per liter of reaction mixture. Acetaldehyde may be added by several means. In one aspect the acetaldehyde is added to the reaction mixture in one batch or more batches or alternatively continuously. Acetaldehyde may be premixed with compound of formula III and added to the reaction mixture. The total amount of acetaldehyde added to the reaction mixture is from about 0.1 to about 4 molar equivalents to total amount of acceptor substrate (compound III), in particular from about 1 to about 3 molar equivalents, more preferably from about 2 do 2.5 molar equivalents. In particular this allows minimal concentrations of undesired products, particularly compounds of formula XII and XIII whereas compound of formula XII is obtained by reacting one molecule of acetaldehyde with one molecule of III and compound of formula XIII is obtained by reacting three molecules of acetaldehyde.

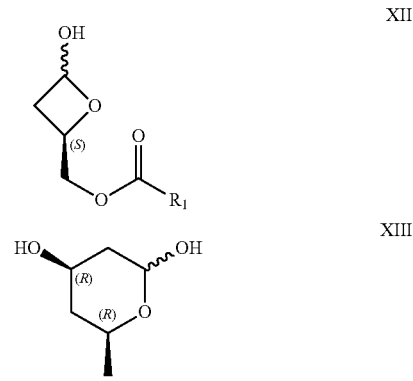

In preferred embodiment the substrates are added continuously to the reaction mixture by means of programmable pump at specific flow rate at any given time of the reaction. The flow rate is determined as maximum flow rate where the substrates are not accumulating in the reaction mixture. In particular this allows minimal concentrations of undesired products. More particularly this products may be compounds of formula XII and XIII. In another embodiment the inhibitory effect of substrates can be further minimized using correct addition strategy.

Alternatively aldolase may be added to reaction mixture containing at least one of compound of formula III or acetaldehyde. The reaction mixture is understood to comprise solvent and at least one of aldolase or compound of formula III or acetaldehyde.

In one aspect, the pH used for aldolase-catalyzed reaction is from about 5 to 10. In one embodiment, the pH used for aldolase-catalyzed reaction is from about 5 to about 8. Specifically, the pH will be maintained by a suitable buffer in the range of 5 to 7.

Some commonly used buffers can lower the yield of the aforementioned aldolase-catalysed reaction by limiting availability of aldolase-condensation intermediates particularly, first condensation reaction products as they may undergo chemical reaction with the buffer. We discovered that bis-tris propan reacts with said intermediates. Other buffers that may react similarity are bis-tris, tricin, tris, bicin or any other buffer having primary, secondary or tertiary amino group. Thus a suitable buffers for adjusting the pH-value, if this adjustment is needed, are made with acids, bases, salts or mixtures thereof in particular phosphoric acid and sodium hydroxide.

In one aspect, the temperature used for aldolase-catalyzed reaction is from about 20 to about 70° C. In one embodiment, the temperature used for aldolase-catalyzed reaction is from about 25 to about 60° C. In one embodiment the temperature used for aldolase-catalyzed reaction is from about 30 to about 50° C.

The reaction is industrially suitable, as it proceeds to completion within few hours.

After the completion of the reaction, the enzyme is removed from the reaction mixture by the addition of at least about 1 vol. of acetonitrile to 1 vol. of the reaction mixture. Alternatively, the enzyme is removed by any precipitation method known in the art. In one embodiment, the precipitation is performed with the addition of ammonium sulfate of at least 5% m/V. Alternatively, the IV is extracted by salting out methods known in the art. Particularly, the salting out is performed by adding at least about 1 vol. of acetonitrile to 1 vol. of the reaction mixture and 5% (m/V) of NaCl. The mixture is then cooled to at least 4° C. and the liquid phases are allowed to separate. The acetonitrile phase is then evaporated to yield the crude product of IV. Alternatively the whole cell catalyst is removed from the reaction mixture using sedimentation techniques, particularly centrifugation. In another aspect, the whole cell catalyst can be removed by filtration techniques, in particular by microfiltration.

The invention also provides a purification method for obtaining pure lactols produced by the reaction. In one aspect, the acetonitrile is evaporated from the reaction mixture and the aqueous solution remaining is then lyophilized. In another aspect, the supernatant of the sedimented either precipitation solution or whole cell catalyst suspension is lyophilized. The powdered remain is then suspended in acetonitrile/diisopropyl ether 1:1. The suspension is filtered to remove insoluble salts and the filtrate is loaded to a silicagel column using acetonitrile/diisopropyl ether 1:1 as the mobile phase. In another aspect, the acetonitrile phase from salting out extraction is evaporated and the remaining oil is dissolved in a minimum volume of acetonitrile/diisopropyl ether 1:1 and loaded to a silicagel column using acetonitrile/diisopropyl ether 1:1 as the mobile phase.

In a particular embodiment, the invention provides for the reaction of $CH_3CO_2CH_2CHO$ with acetaldehyde under aldolase-catalysed aldol condensation conditions to form ((2S,4R)-4,6-dihydroxytetrahydro-2H-pyran-2-yl)methyl acetate, wherein the used aldolase is DERA 01, DERA 02 in an appropriate solvent (in particular aqueous solvent, which may be water in mixture with water soluble organic solvent) in pH range from 5 to 10, in particular 5 to 8 (adjusted if needed with acids, bases, salts or mixtures thereof in particular with phosphoric acid and sodium hydroxide), wherein the reaction proceeds at temperature around 35-40° C. and the conversion is finished in 1 to 6 hours.

In general, aldolase used is prepared by methods of protein expression described in Sambrook, et al. (1989) Molecular cloning: A laboratory Manual $2^{nd}$ Edition, New York: Cold Spring Harbor Laboratory Press, Cold Spring Harbor. Gene coding aldolase is cloned into an expression vector and the enzyme is expressed in a suitable expression host.

The reaction yields are calculated relatively to total amount of compound of formula III added to the reaction mixtures and they are determined as ratio between moles of isolated product and moles of compound of formula III added to the reaction mixture.

The invention also provides for the process for preparing a compound of formula XV

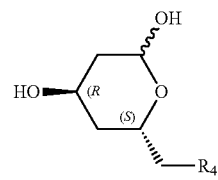

XV wherein $R_4$=$OCOR_1$ (wherein $R_1$ is as defined above), chloride, hydrogen, allyloxy and benzyloxy respectively and independently substituted or not substituted, which comprises the step of bringing in contact acetaldehyde and an aldehyde of the formula XIV, $R_4CH_2CHO$ wherein $R_4$ is defined as above, with microorganism or a part of microorganism, respectively, over expressing biologically active form of aldolase. Preferably $R_4$ is acetate, chloride or hydrogen, more preferably $R_4$ is acetate.

Said contacting step is performed such that aldol condensation is catalysed. Therefor aldolase over expressing organism as whole cell catalysts is used. Preferably enzyme in the form of whole cell catalyst is 2-Deoxyribose-5-phosphate aldolase (DERA, EC 4.1.2.4) as defined above.

Said whole cell catalyst is preferably selected from Bacteria and Yeast over expressing biologically active form of an aldolase. Bacteria is preferably selected from the group of genera consisting of *Escherichia, Corynebacterium, Pseudomonas, Streptomyces, Rhodococcus, Bacillus*, and *Lactobacillus*, more preferably *Escherichia coli* is used. Yeast is preferably selected from the group of genera consisting of *Saccharomyces, Pichia, Shizosaccharomyces* and *Candida*.

In a particular aspect of the present invention, Rosuvastatin can be prepared according to WO 2007/039287 A1 starting from our compound of formula VI as disclosed on following scheme:

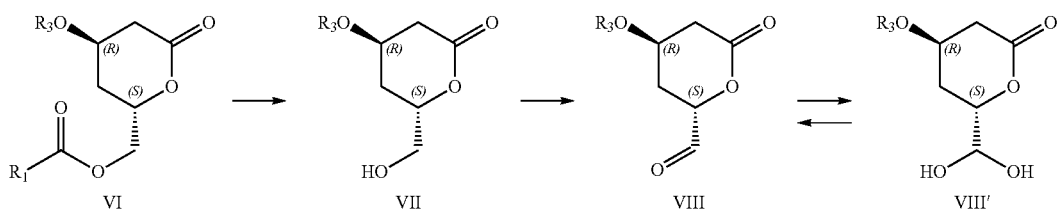

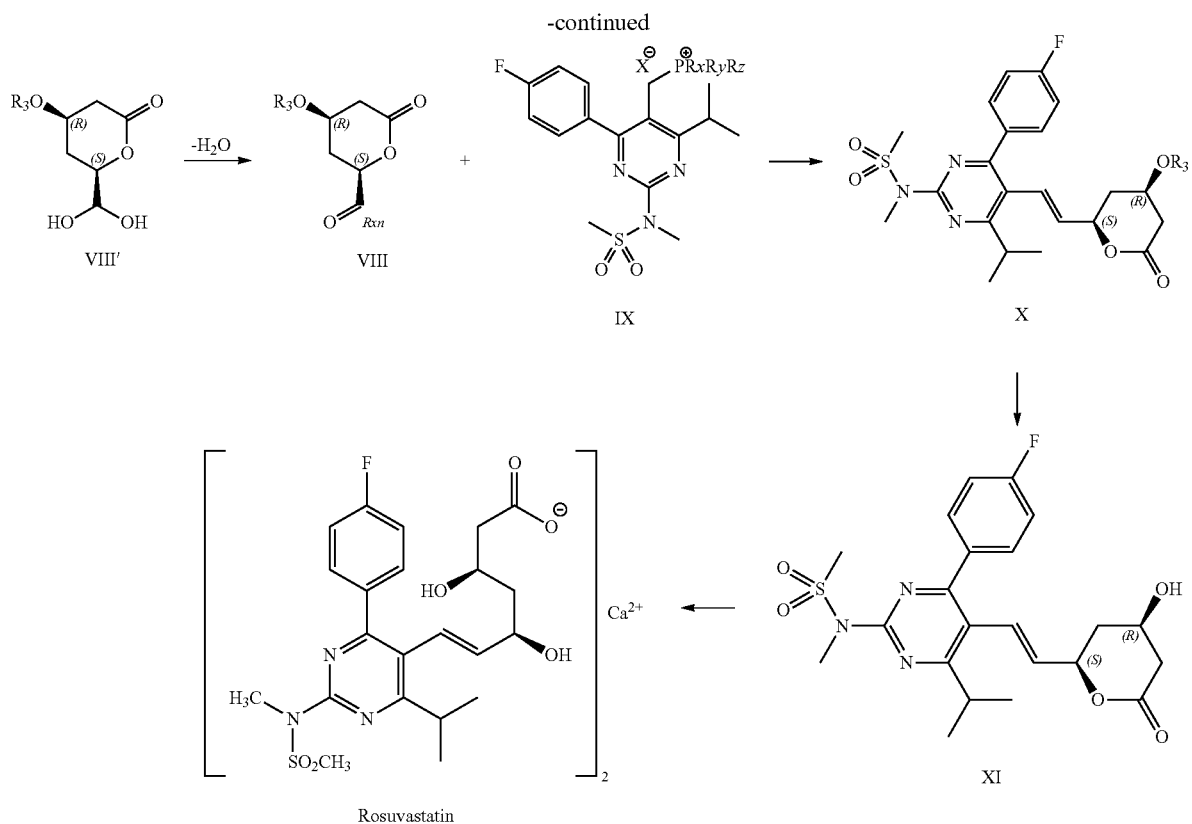

To produce rosuvastatin or other statins, compound of formula VI is transformed in two steps (via compound of formula VII) to (2S,4R)-4-(protected)-6-oxo-tetrahydro-2H-pyran-2-carbaldehyde VIII or its hydrate VIII'. Aldehyde VIII or its hydrate VIII' can be reacted under condition of a Wittig coupling with an appropriate reagent followed by hydrogenation when needed.

The appropriate reagent is a heterocyclic or alicyclic derivative (skeleton of a statin) of a following formula:

where A can be a bond or O;

and wherein $R_x$, $R_y$, and $R_z$, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl;

and X is an anion, preferably a halogen or carboxylate anion, more preferably chloride, bromide or trifluoroacetate;

and Het is selected so that it forms a heterocyclic or alicyclic skeleton of a statin;

other HMG-CoA reductase inhibitors (preferably selected among cerivastatin, fluvastatin, pitavastatin, bervastatin, dalvastatin) can be analogously prepared.

The heterocyclic or alicyclic skeleton (Het) of a statin is in particular selected from:

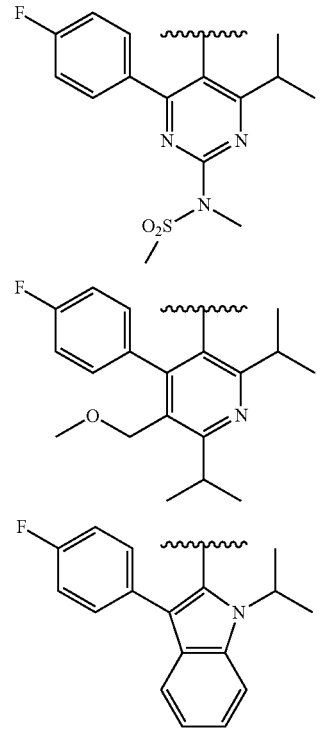

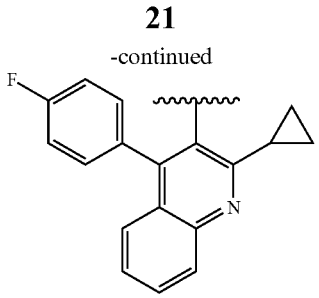

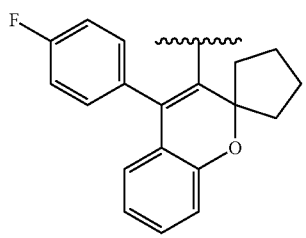

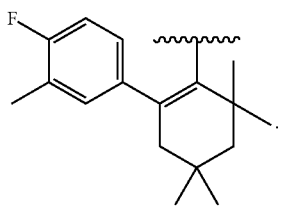

The following examples illustrate the process of the present invention and are not intended to limit the scope of the invention:

Example 1

Acetoxyacetaldehyde (III)

1. Step:

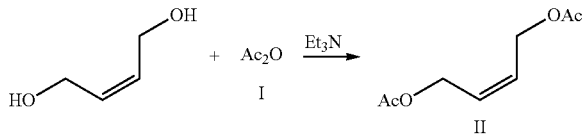

1,4-Dihydroxybut-2-ene (10 mL, 0.12 mol, 1 eq) was dissolved in triethylamine (67 mL, 4 eq). The solution was cooled down to 0° C. and acetic anhydride (I) (34 mL, 3 eq) was added dropwise. The resulting reaction mixture was warmed-up to room temperature and was stirred overnight.

The solution was washed twice with 1M $H_3PO_4$ solution (60 mL), twice with $NaHCO_3$ 1M solution (60 mL). Then, the solution was dried over $MgSO_4$ and concentrated. Traces of AcOH and $Ac_2O$ were removed using a high vacuum pump at 70° C.

Pure II was obtained as a pale yellow to dark liquid (20.6 g, 100%). $^1H$ NMR (300 MHz, $CDCl_3$) δ 5.65 (m, 2H), 4.58 (m, 4H), 1.97 (s, 6H), $^{13}C$ NMR (75 MHz, $CDCl_3$) δ 170.2, 127.6, 59.5, 20.2.

2. Step:

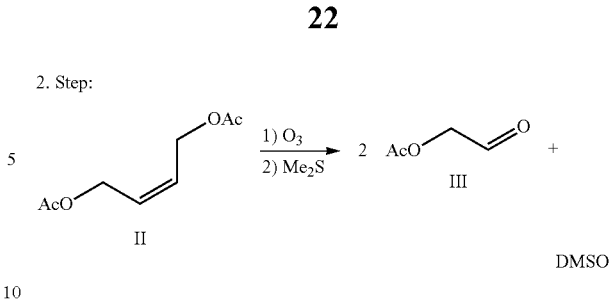

1,4-diacetoxybut-2-ene (II) (1.7 g, 10 mmol, 1 eq) was dissolved in dichloromethane (0.17M). Oxygen (or dry air) sparge was turned on (around 10 L/h) and solution was cooled down to −80° C. Once at −80° C., the ozonator was turned on and ozone was bubbled until the solution turned blue. The ozonator was then turned off and oxygen (or dry air) was bubbled until the blue colour disappeared. Argon was bubbled for 10 min. The sparge was removed and solution was kept under argon at −80° C. Methylsulfide (1.8 mL, 2.5 eq) was added dropwise and the reaction was warmed-up to room temperature and stirred for 20 h. Reaction was concentrated to give a 2:1 mixture of 1,4-acetoxyacetaldehyde (III) and DMSO. The yield assumed to be quantitative, no trace of 1,4-diacetoxybut-2-ene. Product was used without any further purification. (III) $^1H$ NMR (300 MHz, $CDCl_3$) δ 9.51 (s, 1H), 4.59 (s, 2H), 2.10 (s, 3H), 2.58 (s, DMSO)

Example 2

Preparation of Aldolase

*Escherichia coli* gene deoC has been amplified using oligonucleotide primers

```
CGGGATCCACTGATCTGAAAGCAAGCAGCC
and
GCAAGCTTGCTGCTGGCGCTCTTACC
```

(having a SEQ ID No. of 48 and 49, respectively) in a PCR reaction using an isolated genome DNA from the *E. coli* K-12 strain. The product was cleaved with restriction endonucleases BamHI and HindIII and the resulting fragment has been separated on agarose gel electrophoresis and purified. An expression vector pQE30 (Qiagene inc., Valencia, Calif., USA) has been cleaved using the same beforementioned restriction endonucleases and purified. The fragments have been assembled in a T4 ligase reaction. Competent *Escherichia coli* DH5alpha cells were transformed with the above mentioned ligation reaction. Ampicillin resistant colonies were cultured and plasmid DNA has been isolated. The resulting construct has been designated pQE30DeraC and sequenced for conformation of the gene sequence. Aldolase expressing organism has been prepared by transforming competent *Escherichia coli* TOP10 F' strain (Invitrogen corp., Carlsbad, Calif., USA) with the vector pQE30DeraC. The methods used for the process are described in Sambrook et al. (1989) Molecular cloning: A Laboratory Manual $2^{nd}$ Edition, New York: Cold Spring Harbor Laboratory Press, Cold Spring Harbor and are well known to a skilled person.

Terrific Broth media (150 mL, 12 g/L bacto tryptone, 24 g/L bacto yeast extract, 4 mL/L glycerol, 2.31 g/L $KH_2PO_4$, 12.54 g/L $K_2HPO_4$) supplemented with ampicillin (100 μg/mL) was inoculated with 3 mL of TOP10 F' PQE30DeraC overnight culture. Cells were grown (37° C., 250 rpm) until $OD_{600}$ reached approx. 0.8. Protein expression was induced with IPTG (1 mM final concentration) and cells were left in the same growing conditions for additional 4 h. The cell pellet was harvested by centrifugation (10 min, 6000 g, 4° C.). The supernatant was removed and replaced by same volume of buffer (50 mM NaH$_2$PO$_4$, pH 7.0, 300 mM NaCl). The pellet was resuspended and collected again by centrifugation (10 min, 6000 g, 4° C.). The supernatant was removed and cells were stored at −20° C. before use. The whole cell catalyst with DERA 01 was thus obtained.

Alternatively the pellet was resuspended in lytic buffer (50 mM NaH$_2$PO$_4$, pH 7.0, 300 mM NaCl, 2 mM DTT) using 200 g of pellet per 1 L of said buffer. Cells were sonified (3×15 s) using Branson digital sonifier and cell debris was removed by sedimentation (10 min, 20 000 g, 4° C.). A clear aqueous solution of DERA 01 was thus obtained.

Example 3

((2S,4R)-4,6-dihydroxytetrahydro-2H-pyran-2-yl) methyl acetate (IV)

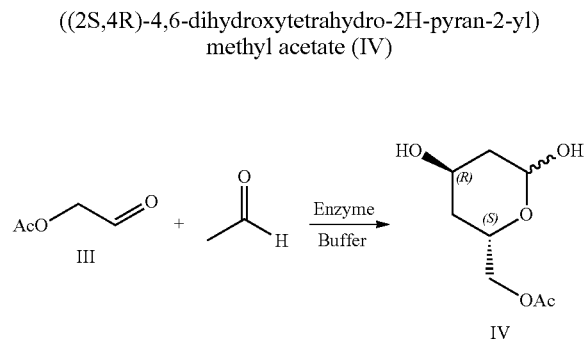

600 mL of solution of DERA 01, 200 mL of reaction buffer (50 mM NaH$_2$PO$_4$, pH 7.0, 300 mM NaCl in water), 100 mL of solution of acetaldehyde (1.05M solution in reaction buffer) and 100 mL of III' (500 mM solution in reaction buffer) were mixed in a stirred reaction vessel giving 1 L of the reaction mixture. The pH-value of the mixture was corrected to 7.0 using 1M aqueous solution of NaOH. The mixture was incubated for 3 hours in a temperature controlled bath set at 37° C. During the reaction, the production of IV was monitored using LC-MS analysis On Triple-quadropole HPLC-UV-MS/MS system with ESI ionization using Synergy Fusion, 250×4.6 mm, 4 μm column. The cromatography conditions were as follows: $T_{column}$=50° C., Flow: 1.5 ml/min, $V_{inj}$=50 μl. Mobile phases were used in following manner:
A: 0.1% (m/v) NH4CH$_3$COO in water pH=6.5
B: Milli Q water
C: Acetonitrile
Linear gradient:

| Time (min) | % A | % B | % C |
|---|---|---|---|
| 0.0 | 20 | 80 | 0 |
| 4.0 | 20 | 80 | 0 |
| 8.0 | 20 | 0 | 80 |
| 12.0 | 20 | 0 | 80 |

Growing of a peak area with RT=7.7+−0.5 min and a mass of 208 (representing M+NH$_4$$^+$) has been observed during the reaction, but not in any of the controls each having one component of reaction mixture replaced with the reaction buffer.

The reaction was quenched using 4 L of acetonitrile and addition of 50 g of NaCl. The suspension was cooled down to 0° C. and the liquid phases were separated by centrifugation (10 min, 6000 g, 4° C.). The upper phase was removed and evaporated under reduced pressure giving 8.4 g of pale yellow oil (crude product). The crude product was purified on a silica gel column (Mobile phase: acetonitrile/diisopropyl ether=1/1). Thereafter, the solution was evaporated under reduced pressure to give 2.4 g of product IV.

(IV): $^1$H NMR (300 MHz, CDCl$_3$) δ 5.39 (d, 1H), 4.53 (m, 1H), 4.29 (m, 1H), 4.14 (m, 2H), 2.11 (s, 3H), 2.04-1.60 (m, 4H), $^{13}$C NMR (75 MHz, DMSO-d$_6$) δ170.8, 91.7, 68.1, 66.8, 63.3, 33.9, 20.7

Example 4

((2S,4R)-4,6-dihydroxytetrahydro-2H-pyran-2-yl) methyl acetate (IV)

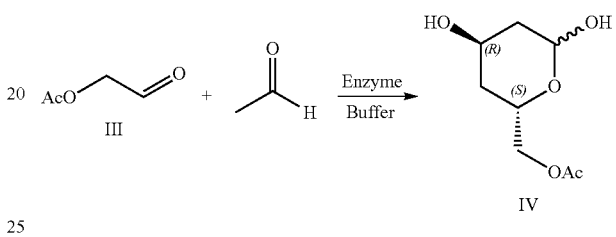

The whole cell catalyst with DERA 01 (300 g) was suspended in 750 mL of reaction buffer (50 mM NaH$_2$PO$_4$, pH 7.0, 300 mM NaCl in water) and incubated in a stirred vessel with controlled temperature set at 37° C. 750 mL of substrate solution (630 mM acetaldehyde (III), 300 mM solution in reaction buffer) were added during the 2 h reaction time using a calibrated peristaltic pump. pH was controlled at 7.0 using 1M aqueous solution of NaOH. The reaction was allowed to continue for another 30 min., and then the whole cell catalyst was sedimented by centrifugation (10 min, 6000 g, 4° C.). The supernatant was then lyophilized to give 19.4 g of pale yellow crystals (crude product). The crude product was purified on a silica gel column (Mobile phase: acetonitrile/diisopropyl ether=1/1). Thereafter the solution was evaporated under reduced pressure to give 7.4 g of product IV.

(IV): $^1$H NMR (300 MHz, CDCl$_3$) δ 5.39 (d, 1H), 4.53 (m, 1H), 4.29 (m, 1H), 4.14 (m, 2H), 2.11 (s, 3H), 2.04-1.60 (m, 4H), $^{13}$C NMR (75 MHz, DMSO-d$_6$) δ 170.8, 91.7, 68.1, 66.8, 63.3, 33.9, 20.7.

During the reaction, the production of IV was monitored using LC-MS analysis. Growing of a peak area with a mass of 208 (representing M+NH$_4$$^+$) has been observed during the reaction and quantitative analysis of the reaction mixture after 2.5 hours with LC-MS showed presence of 13.1 g/L of IV.

Example 5

((2S,4R)-4,6-dihydroxytetrahydro-2H-pyran-2-yl) methyl acetate (IV)

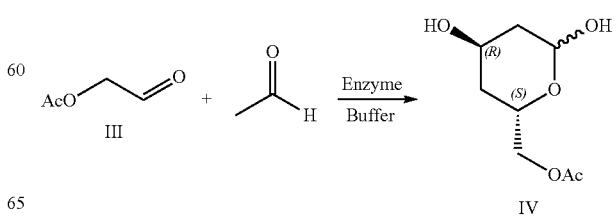

The whole cell catalyst with DERA 02 (3 g) was suspended in 6 mL of the reaction buffer (50 mM NaH$_2$PO$_4$, pH 7.0, 300 mM NaCl in water). 2 mL of solution of acetaldehyde (2.1M solution in the reaction buffer) and 2 mL of III (1M solution in the reaction buffer) were mixed in a reaction tube giving 10 mL of the reaction mixture. The pH-value of the mixture was corrected to 7.0 using 1 M aqueous solution of NaOH. The mixture was incubated for 3 hours in a temperature controlled bath set at 37° C. During the reaction, the production of IV was monitored using LC-MS analysis. Growing of a peak area with a mass of 208 (representing M+NR$_4^+$) has been observed during the reaction, but not in any of the controls each having one component of reaction mixture replaced with reaction buffer and quantitative analysis of the reaction mixture after 1 hour with LC-MS showed presence of 8.7 g/L of IV.

Example 6

((2S,4R)-4,6-dihydroxytetrahydro-2H-pyran-2-yl)methyl acetate (IV)

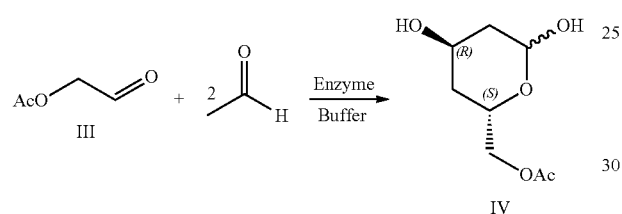

56.6 g of III (92%) was diluted in 1070 mL reaction buffer (50 mM NaH$_2$PO$_4$, pH 7.0, 150 mM NaCl). The pH value of this solution was adjusted to 6.2 with NaHCO$_3$ salt. 510 mL of the whole cell catalyst with DERA 01 (700 g/L) was added to previous solution and the pH value was again corrected to 6.2 with NaHCO$_3$ salt. The mixture was incubated for 3 hours in a temperature controlled 2-L bioreactor set at 37° C. and 800 rpm of constant stirring. 120 mL of acetaldehyde (45.4 g) diluted in the reaction buffer was added with programmable pump to the reaction mixture continuously in 3 hours time span as described in the table below:

| Time [min] | 0 | 5 | 10 | 15 | 20 | 25 | 30 | 35 | 45 |
|---|---|---|---|---|---|---|---|---|---|
| Volume of added acetaldehyde [mL] | 0 | 15 | 27 | 38 | 47 | 54 | 60 | 65 | 73 |
| Flow [mL/min] | 3.000 | 2.400 | 2.200 | 1.800 | 1.400 | 1.200 | 1.000 | 0.800 | 0.600 |
| Time [min] | 60 | 75 | 90 | 105 | 120 | 135 | 150 | 165 | 180 |
| Volume of added acetaldehyde [mL] | 82 | 90 | 96 | 102 | 106 | 110 | 114 | 117 | 120 |
| Flow [mL/min] | 0.533 | 0.400 | 0.400 | 0.267 | 0.267 | 0.267 | 0.200 | 0.200 | 0 |

During the reaction the pH was not corrected and drifted slowly down to 5.5 end value. The production of IV was monitored using GC analysis (chromatographic column: DB-1 100% dimethylpolysiloxane; temperature program: initial temperature: 50° C., initial time: 5 min, temperature rate: 10° C./min, final temperature: 215° C., final time: 10 min; injector: split/splitless injector, carrier gas: helium, initial flow: 10 mL/min; detector: flame-ionization detector, detector temperature: 230° C.; chromatographic solutions: 1-5 mg of IV/mL acetonitrile) by monitoring retention times at 5.17 min (compound III), 14.04 min (compound XII), 14.44 min compound (compound XIII) and 20.35 min (compound IV). The reaction profile is shown in FIG. 1.

Quantitative analysis of the reaction mixture after 3 hours with GC showed 35.3 g/L of IV with 67.7% molar yield. Analysis of enantiomeric purity of compounds in further synthetic steps derived from the material described in example 6 showed enantiomeric excess of 99.8% or more which indicates very high enantiomeric purity of this material. Analysis of diastereomeric purity of compounds in further synthetic steps derived from the material described in example 6 showed diastereomeric excess of 98% or more which indicated as well a high diastereomeric purity of IV.

Example 7

((2S,4R)-4-hydroxy-6-oxotetrahydro-2H-pyran-2-yl)methyl acetate (V)

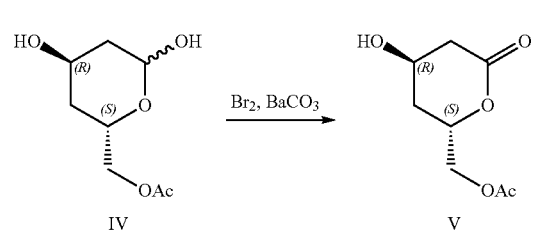

The solution of ((2S,4R)-4,6-dihydroxytetrahydro-2H-pyran-2-yl)methyl acetate (IV) (1 eq) in water was cooled down to 0° C. Barium carbonate (1.4 eq) was added followed by a dropwise addition of Br$_2$ (1.2 eq) and the reaction was stirred overnight at room temperature. The solution was saturated with NaCl and extracted four times with EtOAc. The combined organic phases were dried over MgSO$_4$ and concentrated. The purification using flash chromatography (hexane/acetone=75/25 to 55/45) furnished ((2S,4R)-4-hydroxy-6-oxotetrahydro-2H-pyran-2-yl)methyl acetate (V).

(V): $^1$H NMR (300 MHz, acetone-d$_6$) δ 4.88 (m, 1H), 4.45 (d, J=3.0 Hz, 1H), 4.38 (hex, J=3.0 Hz, 1H), 4.23 (dd, J=3.5 Hz, J=12.0 Hz, 1H), 4.16 (dd, J=5.5 Hz, J=12.1 Hz, 1H), 2.68 (dd, J=4.3 Hz, J=17.5 HZ, 1H), 2.51 (dddd, J=0.8 Hz, J=2.0

Hz, J=3.3 Hz, J=17.5 Hz, 1H), 2.03 (s, 3H), 1.91 (m, 2H), $^{13}$C NMR (75 MHz, acetone-$d_6$) δ 170.8, 169.7, 74.2, 66.5, 62.7, 39.1, 32.3, 20.6.

Example 8

((2S,4R)-4-(tert-butyldimethylsilyloxy)-6-oxotetrahydro-2H-pyran-2-yl)methyl acetate (VI)

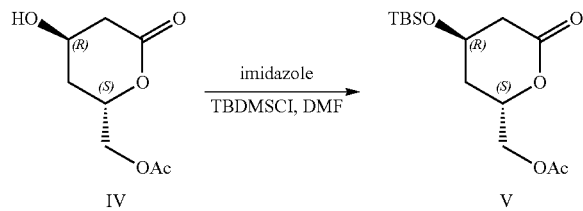

The solution of ((2S,4R)-4-hydroxy-6-oxotetrahydro-2H-pyran-2-yl)methyl acetate (V) (1.88 g, 10 mmol, 1 eq) was dissolved in dry DMF (2 mL, 1M). Imidazole (0.88 g, 1.3 eq) and TBDMSCI (1.66 g, 1.1 eq) were successively added and the reaction was stirred until the completion of the reaction. The reaction mixture was partitioned between water (20 mL) and ether (20 mL). The aqueous phase was extracted once with ether (20 mL). The combined organic phases were washed twice with a small amount of water (10 mL), with HCl 1N (20 mL) and with brine (20 mL). The solution was dried over $MgSO_4$ and concentrated to furnish ((2S,4R)-4-(tert-butyldimethylsilyloxy)-6-oxotetrahydro-2H-pyran-2-yl)methyl acetate (VI) in a quantitative yield. $^1$H NMR (300 MHz, $CDCl_3$) δ 4.93 (m, 1H), 4.37 (quint, J=3 Hz, 1H), 4.30 (dd, J=3 Hz, J=12 Hz, 1H), 4.21 (dd, J=5 Hz, J=12 Hz, 1H), 2.62 (d, J=4 Hz, 2H), 2.11 (s, 3H), 1.84-1.80 (m, 2H), 0.89 (s, 9H), 0.09 (2s, 6H). $^{13}$C NMR (75 MHz, $CDCl_3$) δ 170.4, 169.1, 73.3, 65.5, 63.0, 38.9, 32.2, 20.5, 17.7, −5.1, −5.2.

Example 9

Conversion of ((2S,4R)-4-(tert-butyldimethylsilyloxy)-6-oxotetrahydro-2H-pyran-2-yl)methyl acetate (VI) to (4R,6S)-4-(tert-butyldimethylsilyloxy)-6-(hydroxymethyl)tetrahydro-2H-pyran-2-one (VII) via enzymatic reaction

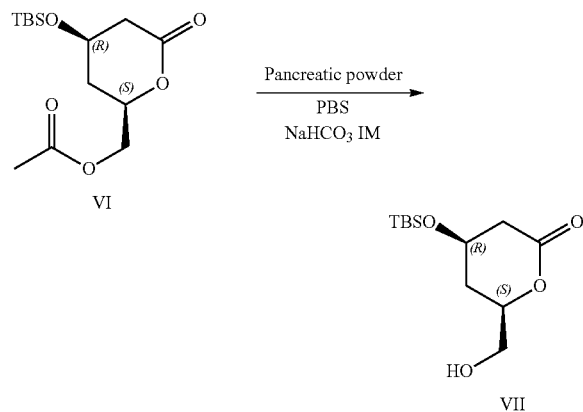

((2S,4R)-4-(tert-butyldimethylsilyloxy)-6-oxotetrahydro-2H-pyran-2-yl)methyl acetate (VI) (50 g, 80% purity; 132.4 mmol) was added to phosphate buffer solution (P.B.S.) pH=5.20 (1.5 L), the solution was warmed up to 37° C. Pancreatin powder (0.5 eq. mass; 20 g) was then added stepwise (6 times, 8 g+3×4 g). In parallel, pH was monitored and was regulated by adding $NaHCO_3$ solution (1M) each hour to maintain pH between 4.85 and 4.95. The reaction was stirred for 9 hours after the first addition of enzyme.

Celite® was added to the crude mixture. The solution was filtered off through Celite®. A pale yellow liquid was recovered. The solid on the filter was washed with 1.5 L of EtOAc. The filtrate was stirred for 5 minutes. The two layers were separated. The water phase was reextracted once with EtOAc (1.5 L). The combined organic phases were partially evaporated under reduced pressure at 40° C. and the product was recrystallized from methylcyclohexan to give 82% of (4R,6S)-4-(tert-butyldimethylsilyloxy)-6-(hydroxymethyl)tetrahydro-2H-pyran-2-one (VII) as white crystals. The conversion of the reaction was almost quantitative (>98%) with less than 0.1% of enantiomer.

GC analysis for determination of enantiomer was done with a DCM solution (2-3 mg/mL) on a Betadex 120 column with a split/splitless injector and a FID detector.

NMR analysis of compound VII didn't show that diastereoisomers are present even with high scan accumulation at detection limit, which indicates that diastereoisomers level in VII is below 1%.

Example 10

Conversion of ((2S,4R)-4-(tert-butyldimethylsilyloxy)-6-oxotetrahydro-2H-pyran-2-yl)methyl acetate (VI) to (4R,6S)-4-(tert-butyldimethylsilyloxy)-6-(hydroxymethyl)tetrahydro-2H-pyran-2-one (VII) via chemical reaction

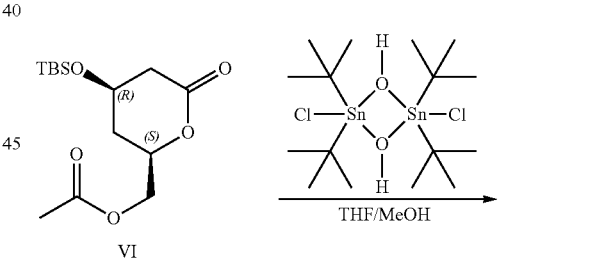

((2S,4R)-4-(tert-butyldimethylsilyloxy)-6-oxotetrahydro-2H-pyran-2-yl)methyl acetate (VI) (0.625 g, 80% purity, 1.65 mmol) was dissolved in THF (8 mL) and MeOH (8 mL). Tin catalyst $(tBu_2SnClOH)_2$ (94 mg, 0.1 eq) was added and the reaction was stirred overnight. Reaction was concentrated and purified by flash chromatography to give pure (4R,6S)-4-(tert-butyldimethylsilyloxy)-6-(hydroxymethyl)tetrahydro-2H-pyran-2-one (VII) (126 mg, 30%). VII was found to contain less than 0.1% of enantiomer.

GC analysis for determination of enantiomer was done with a DCM solution (2-3 mg/mL) on a Betadex 120 column with a split/splitless injector and a FID detector.

NMR analysis of compound VII didn't show that diastereoisomers are present even with high scan accumulation at detection limit, which indicates that diastereoisomers level in VII is below 1%.

The conversion of compound VI to compound VII via enzymatic reaction as well as via chemical reaction gave the product which possessed excellent enantiomeric purity with less than 0.1% of unwanted enantiomer and no difference was observed in enantiomeric purity of compound VII prepared by the two methods. As well, the diastereomeric purity of prepared compound VII was high with less than 1% of unwanted diastereoisomers. The enantiomeric and diastereomeric excess is therefore originating from earlier synthetic steps (e.g. from aldolase catalysed conversion of compound III to compound IV).

---

The invention claimed is:

1. A process for preparing a compound of formula IV

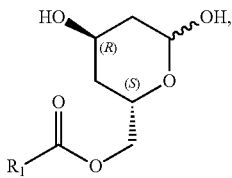

wherein $R_1$=alkyl, alkoxy, aryl, heteroaryl, arylalkyl or heteroarylalkyl, respectively and independently substituted or not substituted, the method comprising the step of bringing into contact acetaldehyde and an aldehyde of the formula III, $R_1CO_2CH_2CHO$, wherein $R_1$=alkyl, alkoxy, aryl, heteroaryl, arylalkyl or heteroarylalkyl, respectively and independently substituted or not substituted, with an enzyme catalyzing aldol condensation.

2. The process according to claim 1, wherein $R_1$=$C_1$-$C_6$ alkyl or alkoxy, respectively and independently substituted or not or $R_1$=$CH_3$.

3. The process according to claim 1, wherein the compound of formula IV has a enantiomeric excess of 98% or more and/or diastereomeric excess of 98% or more.

4. The process according to claim 1, wherein the enzyme is 2-Deoxyribose-5-phosphate aldolase (DERA, EC 4.1.2.4).

5. The process according to claim 1, wherein said enzyme is selected from the group consisting of the following aldolases: DERA 01 comprising a nucleotide sequence of SEQ ID NO: 1 or an amino acid sequence of SEQ ID NO: 2;
  DERA 02 comprising a nucleotide sequence of SEQ ID NO: 3 or SEQ ID NO: 4 or an amino acid sequence of SEQ ID NO: 5;
  DERA 03 comprising a nucleotide sequence of SEQ ID NO: 6 or an amino acid sequence of SEQ ID NO: 7;
  DERA 04 comprising a nucleotide sequence of SEQ ID NO: 8 or an amino acid sequence of SEQ ID NO: 9;
  DERA 05 comprising a nucleotide sequence of SEQ ID NO: 10 or an amino acid sequence of SEQ ID NO: 11;
  DERA 06 comprising a nucleotide sequence of SEQ ID NO: 12 or an amino acid sequence of SEQ ID NO: 13;
  DERA 07 comprising a nucleotide sequence of SEQ ID NO: 14 or an amino acid sequence of SEQ ID NO: 15;
  DERA 08 comprising a nucleotide sequence of SEQ ID NO: 16 or an amino acid sequence of SEQ ID NO: 17;
  DERA 09 comprising a nucleotide sequence of SEQ ID NO: 18 or an amino acid sequence of SEQ ID NO: 19;
  DERA 10 comprising a nucleotide sequence of SEQ ID NO: 20 or an amino acid sequence of SEQ ID NO: 21;
  DERA 11 comprising a nucleotide sequence of SEQ ID NO: 22 or an amino acid sequence of SEQ ID NO: 23;
  DERA 12 comprising a nucleotide sequence of SEQ ID NO: 24 or an amino acid sequence of SEQ ID NO: 25;
  DERA 13 comprising a nucleotide sequence of SEQ ID NO: 26 or an amino acid sequence of SEQ ID NO: 27;
  DERA 14 comprising a nucleotide sequence of SEQ ID NO: 28 or an amino acid sequence of SEQ ID NO: 29;
  DERA 15 comprising a nucleotide sequence of SEQ ID NO: 30 or an amino acid sequence of SEQ ID NO: 31;
  DERA 16 comprising a nucleotide sequence of SEQ ID NO: 32 or an amino acid sequence of SEQ ID NO: 33;
  DERA 17 comprising a nucleotide sequence of SEQ ID NO: 34 or an amino acid sequence of SEQ ID NO: 35;
  DERA 18 is an aldolase comprising a nucleotide sequence of SEQ ID NO: 36 or an amino acid sequence of SEQ ID NO: 37;
  DERA 19 comprising a nucleotide sequence of SEQ ID NO: 38 or an amino acid sequence of SEQ ID NO: 39;
  DERA 20 comprising a nucleotide sequence of SEQ ID NO: 40 or an amino acid sequence of SEQ ID NO: 41;
  DERA 21 comprising a nucleotide sequence of SEQ ID NO: 42 or an amino acid sequence of SEQ ID NO: 43;
  DERA 22 comprising a nucleotide sequence of SEQ ID NO: 44 or an amino acid sequence of SEQ ID NO: 45;
  DERA 23 comprising a nucleotide sequence of SEQ ID NO: 46 or an amino acid sequence of SEQ ID NO: 47; and an aldolase having an amino acid sequence identity of at least about 70% to amino acid sequence of any of said aldolases.

6. The process according to claim 4, wherein said aldolase is selected from the group consisting of:
an amino acid sequence identity of at least about 70% to amino acid sequence of SEQ ID NO: 2;
an amino acid sequence identity of at least 80% to amino acid sequence of SEQ ID NO: 5;
an amino acid sequence identity of at least 80% to amino acid sequence of SEQ ID NO: 11;
an amino acid sequence identity of at least 80% to amino acid sequence of SEQ ID NO: 25; and
an amino acid sequence identity of at least 80% to amino acid sequence of SEQ ID NO: 27.

7. The process according to claim 1, wherein the pH for aldolase-catalysed aldol condensation is maintained in a range of 4.5 to 10, or 5 to 10, or the pH is maintained with a buffer in pH range 5 to 8.

8. The process according to claim 1, wherein a phosphate buffer is used for catalyzing aldol condensation.

9. A process for preparing a compound of formula V

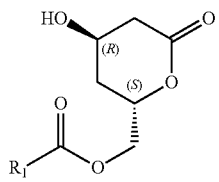

wherein $R_1$=alkyl, alkoxy, aryl, heteroaryl, arylalkyl or heteroarylalkyl, respectively and independently substituted or not substituted, which process comprises the step of converting the compound of formula IV

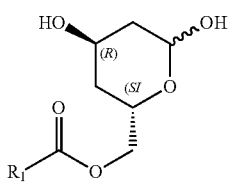

by oxidation into the compound of formula V.

10. The process according to claim 9, wherein the oxidation is performed with $Br_2$ and $BaCO_3$.

11. A compound of formula IV

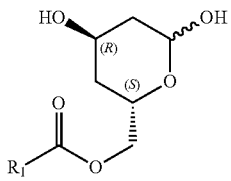

wherein $R_1$=alkyl, alkoxy, aryl, heteroaryl, arylalkyl or heteroarylalkyl, respectively and independently substituted or not substituted.

12. The compound of claim 11, wherein $R_1$=$C_1$-$C_6$ alkyl or alkoxy, or $R_1$=$CH_3$.

13. A process according to claim 1, wherein said step of bringing in contact acetaldehyde and aldehyde of the formula III is accomplished by contacting acetaldehyde and said aldehyde with a microorganism or a part of microorganism, respectively, over expressing biologically active form of aldolase.

14. A process for preparing compound of formula XV

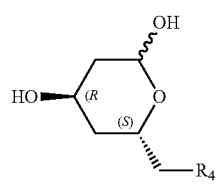

wherein $R_4$=$OCOR_1$, (wherein $R_1$=alkyl, alkoxy, aryl, heteroaryl, arylalkyl or heteroarylalkyl, respectively and independently substituted or not substituted), chloride, hydrogen, allyloxy and benzyloxy respectively and independently substituted or not substituted, which comprises the step of bringing in contact acetaldehyde and an aldehyde of the formula XIV, $R_4CH_2CHO$ wherein $R_4$=$OCOR_1$ (wherein $R_1$=alkyl, alkoxy, aryl, heteroaryl, arylalkyl or heteroarylalkyl, respectively and independently substituted or not substituted), chloride, hydrogen, allyloxy and benzyloxy respectively and independently substituted or not substituted, with a microorganism or a part of microorganism, respectively, that over-expresses a biologically active form of aldolase.

15. The process according to claim 13 wherein the contacting step is performed such that aldol condensation is catalysed.

16. A process according to claim 1, wherein said enzyme is in the form of whole cell catalyst, wherein said whole cell catalyst is a microorganism that over-expresses a biologically active form of aldolase.

17. A process for preparing compound of formula XV

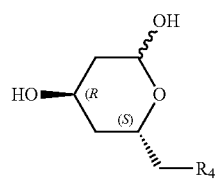

wherein $R_4$=$OCOR_1$ (wherein $R_1$=alkyl, alkoxy, aryl, heteroaryl, arylalkyl or heteroarylalkyl, respectively and independently substituted or not substituted), chloride, hydrogen, allyloxy and benzyloxy respectively and independently substituted or not substituted, which comprises the step of bringing in contact acetaldehyde and an aldehyde of the formula XIV, $R_4CH_2CHO$ wherein $R_4$=$OCOR_1$ (wherein $R_1$=alkyl, alkoxy, aryl, heteroaryl, arylalkyl or heteroarylalkyl, respectively and independently substituted or not substituted), chloride, hydrogen, allyloxy and benzyloxy respectively and independently substituted or not substituted, with an enzyme catalyzing aldol condensation, wherein said enzyme is in the form of whole cell catalyst, wherein said whole cell catalyst is a microorganism that overexpresses a biologically active form of aldolase.

18. The process according to claim 13, wherein said microorganism is Bacteria.

19. The process according to claim 13 wherein said microorganism is Yeast.

20. The compound of formula IV of claim 11, wherein compound has enantiomeric excess of 99.8% or more and/or diastereomeric excess of 98% or more.

21. The process according to claim 18, wherein said Bacteria is selected from the group of genera consisting of *Escherichia, Corynebacterium, Pseudomonas, Streptomyces, Rhodococcus, Bacillus* and *Lactobacillus*.

22. The process according to claim 19, wherein said Yeast is selected from the group of genera consisting of *Saccharomyces, Pichia, Shizosaccharomyces* and *Candida*.

23. The method of claim 21, wherein said bacteria is *Escherichia coli*.

24. The process according to claim 9 wherein said compound of formula V, has a enantiomeric excess of 99.8% or more and/or diastereomeric excess of 98% or more.

* * * * *